US009492550B2

(12) United States Patent
Brugel et al.

(10) Patent No.: US 9,492,550 B2
(45) Date of Patent: Nov. 15, 2016

(54) PHARMACEUTICAL COMPOSITIONS WITH ENHANCED PERFORMANCE AND IMPROVED PROCESSABILITY

(71) Applicant: Hercules Incorporated, Wilmington, DE (US)

(72) Inventors: Todd A. Brugel, Wilmington, DE (US); Tuyen T. Nguyen, Newark, DE (US); Sangrama Sahoo, Wilmington, DE (US); Divya Tewari, West Chester, PA (US); Yuda Zong, West Chester, PA (US)

(73) Assignee: Hercules LLC, Wilmington, DE (US)

( * ) Notice: Subject to any disclaimer, the term of this patent is extended or adjusted under 35 U.S.C. 154(b) by 39 days.

(21) Appl. No.: 14/186,147

(22) Filed: Feb. 21, 2014

(65) Prior Publication Data

US 2014/0249235 A1    Sep. 4, 2014

Related U.S. Application Data

(60) Provisional application No. 61/771,291, filed on Mar. 1, 2013.

(51) Int. Cl.
*A01N 25/00* (2006.01)
*A61K 47/00* (2006.01)
*A61K 9/14* (2006.01)
*C08B 3/06* (2006.01)
*A61K 47/38* (2006.01)
*A61K 31/4418* (2006.01)
*A61K 31/397* (2006.01)
*C08B 13/00* (2006.01)
*C08L 1/32* (2006.01)

(52) U.S. Cl.
CPC ............ *A61K 47/38* (2013.01); *A61K 31/397* (2013.01); *A61K 31/4418* (2013.01); *C08B 13/00* (2013.01); *C08L 1/32* (2013.01)

(58) Field of Classification Search
CPC .......... C08B 13/00; C08L 1/32; A61K 47/38
USPC .................... 424/484, 488; 514/781; 536/69
See application file for complete search history.

(56) References Cited

U.S. PATENT DOCUMENTS

| | | | |
|---|---|---|---|
| 4,226,981 A | 10/1980 | Onda et al. | |
| 4,385,078 A | 5/1983 | Onda et al. | |
| 5,776,501 A | 7/1998 | Kokubo et al. | |
| 6,548,555 B1 | 4/2003 | Curatolo et al. | |
| 8,026,286 B2 | 9/2011 | Curatolo et al. | |
| 8,133,513 B2 | 3/2012 | Hayashi et al. | |
| 8,207,232 B2 | 6/2012 | Babcock et al. | |
| 8,257,741 B2 | 9/2012 | Curatolo et al. | |
| 8,263,128 B2 | 9/2012 | Curatolo et al. | |
| 2006/0159753 A1* | 7/2006 | Ueki .................... | A61K 9/2027 424/468 |
| 2008/0262107 A1 | 10/2008 | Babcock et al. | |
| 2011/0245305 A1 | 10/2011 | Chatterji et al. | |
| 2013/0102691 A1 | 4/2013 | Miller et al. | |

FOREIGN PATENT DOCUMENTS

| | | |
|---|---|---|
| EP | 0219426 A2 | 4/1987 |
| WO | 2011159626 | 12/2011 |
| WO | 2013148154 | 10/2013 |
| WO | 2013154607 | 10/2013 |

OTHER PUBLICATIONS

International Search Report, PCT/US2014/017585 published on Sep. 4, 2014.
Friesen, Dwayne T. et al., Hydroxypropyl Methylcellulose Acetate Succinate-Based Spray-Dried Dispersions: An Overview, Molecular Pharmaceutics, vol. 5, No. 6, pp. 1003-1019, (2008).
Tezuka, Yasuyuki et al., "Determination of substituent distribution in cellulose ethers by means of 13C NMR study on their acetylated derivatives, 4", Makromol Chem, vol. 191, pp. 681-690, (1990).
Tezuka, Yasuyuki et al., "Determination of substituent distribution in cellulose ethers by means of a 13C NMR study on their acetylated derivatives. 1. Methylcellulose", Macromolecules, vol. 20, pp. 2413-2418, (1987).
Curatolo, William et al., Utility of hydroxypropylmethylcellulose acetate succinate (HPMCAS) for imitation and maintenance of drug supersaturation in the GI Milieu.
Grasman, Nick et al., "Impact of Substitution Levels on Spray Dried Dispersions of Hypromellose Acetate Succinate—A Quality by Design Approach".

* cited by examiner

Primary Examiner — Scarlett Goon
(74) Attorney, Agent, or Firm — Dunlap Codding, P.C.; Shaorong Cheng

(57) ABSTRACT

The presently disclosed and claimed inventive concept(s) relates to a polymer for enhancing drug performance and improving processability. Specifically, the polymer comprises hydroxypropyl methyl cellulose acetate succinate (HPMC-AS). On the HPMC-AS, the percentage of total succinoyl degree of substitution is less than 12% at C6-OH position and greater than 53% at C3-OH, and the percentage of total acetyl degree of substitution is greater than 32% at C6-OH position.

5 Claims, 9 Drawing Sheets

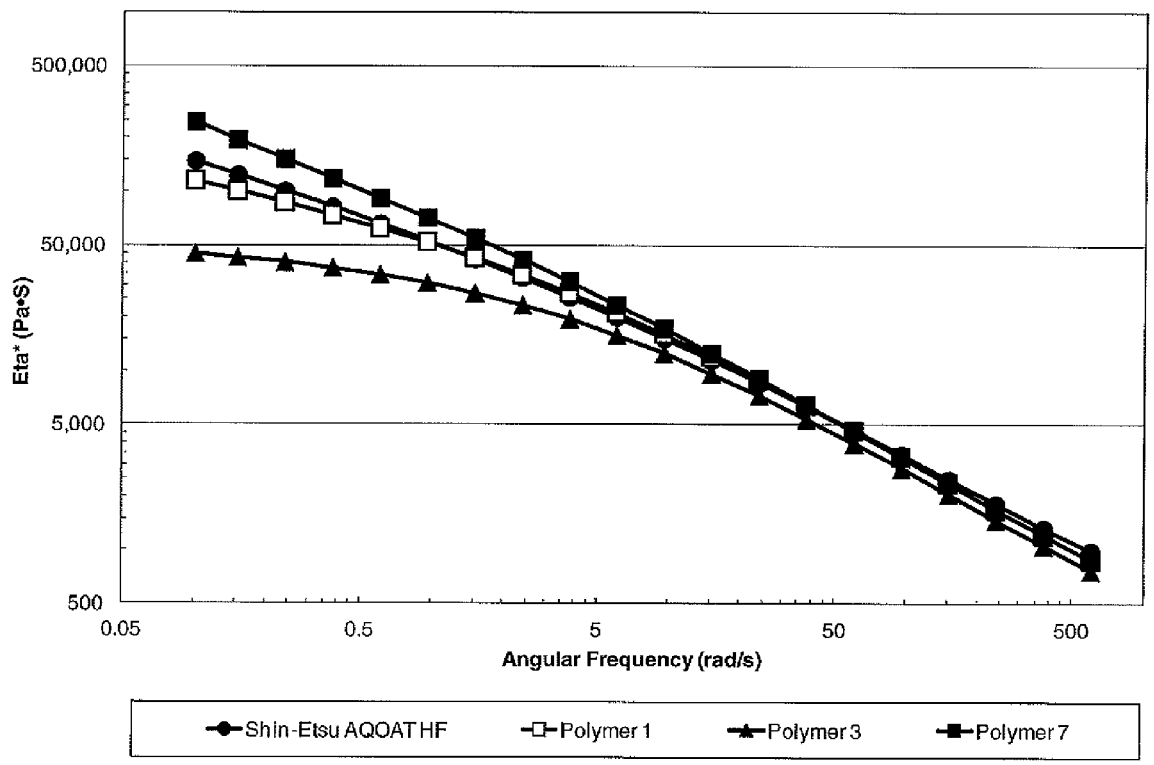
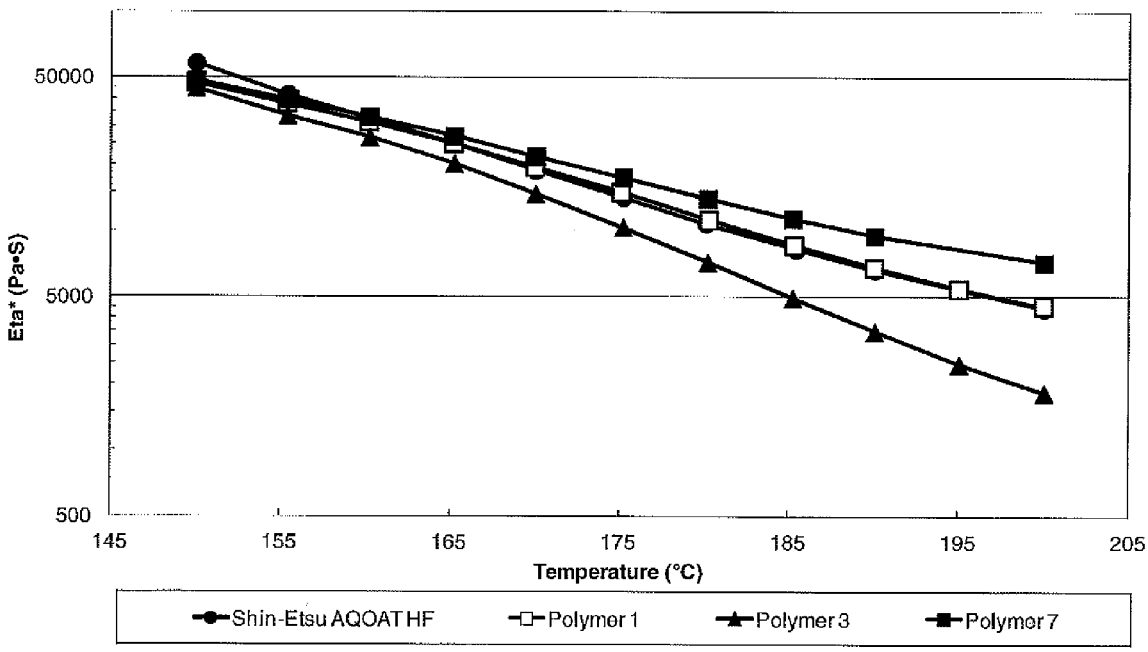

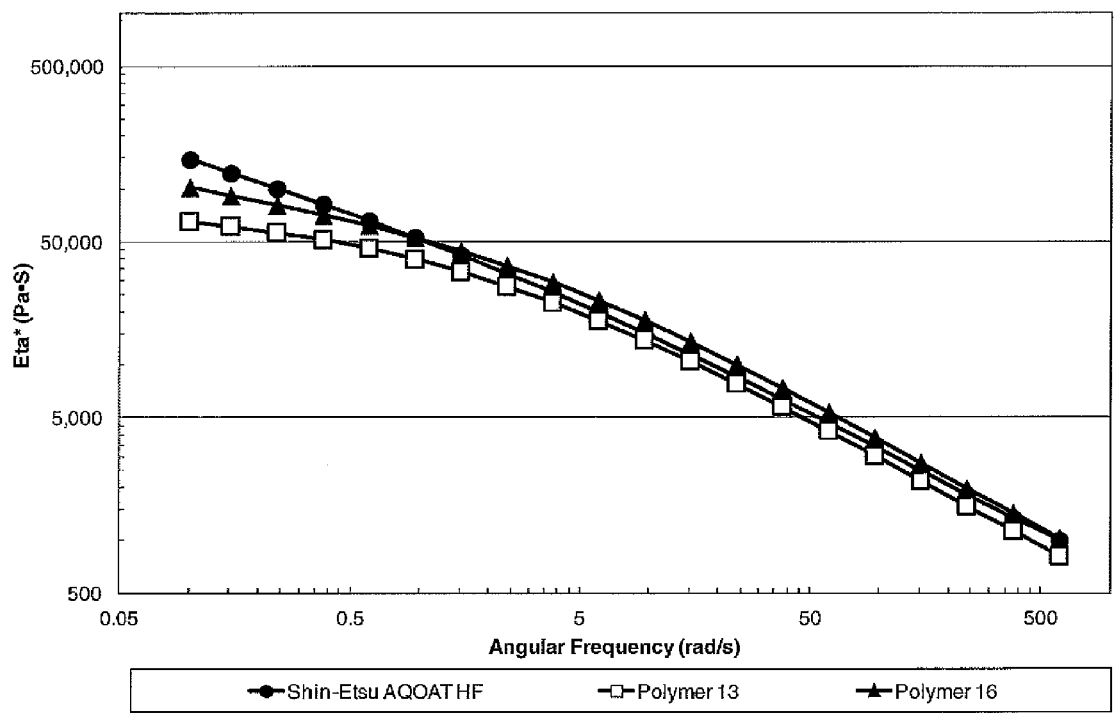
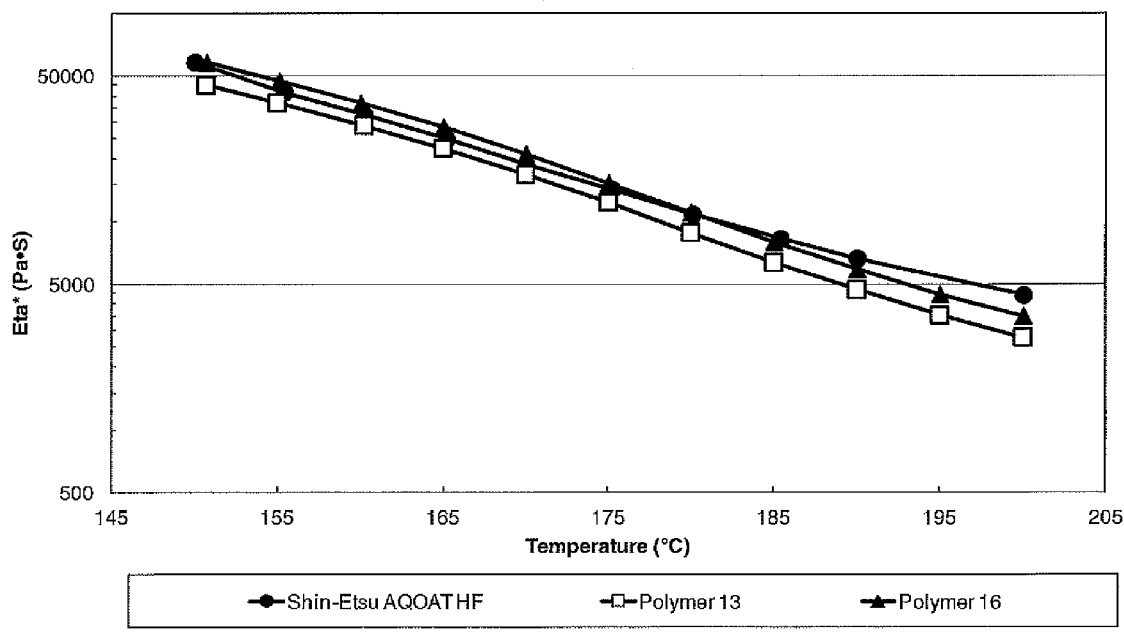

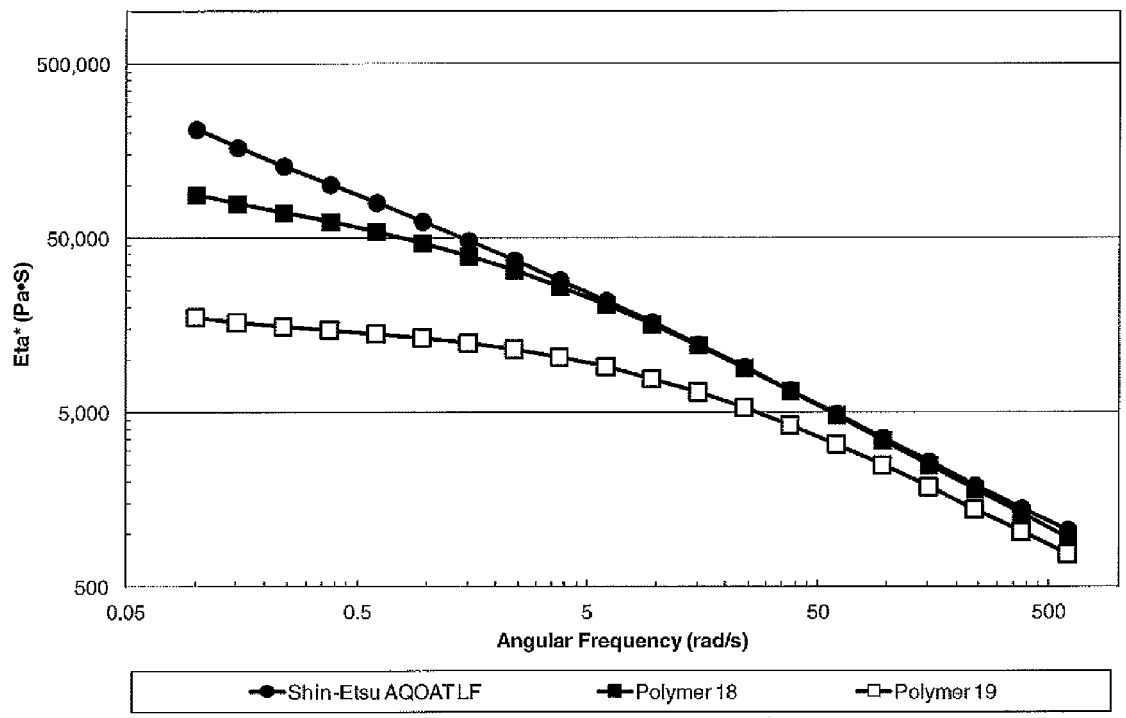
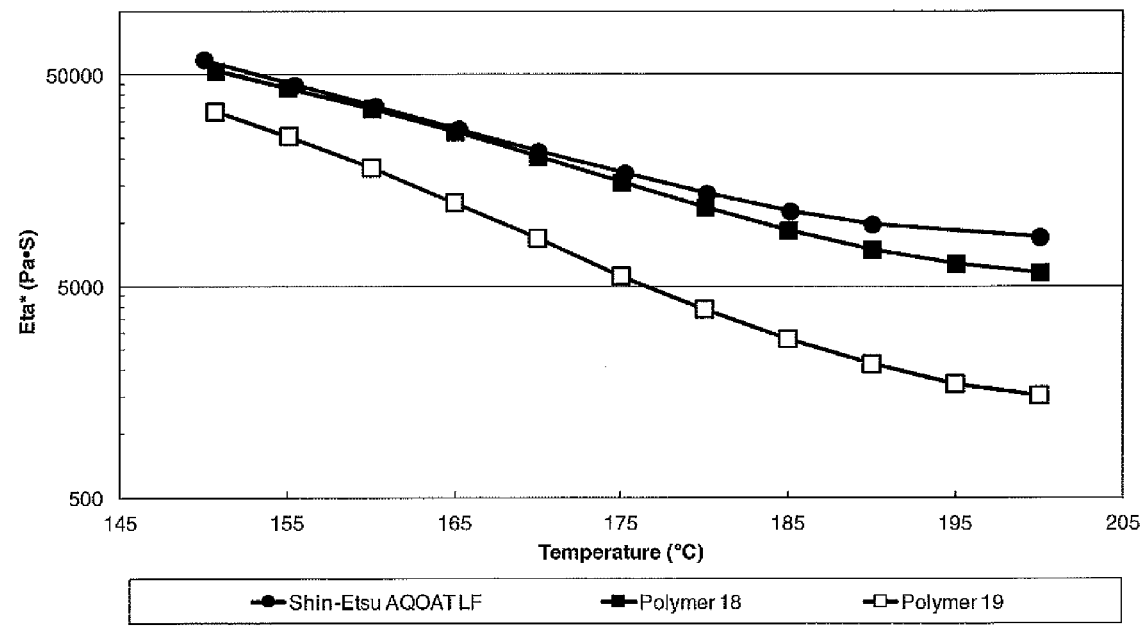

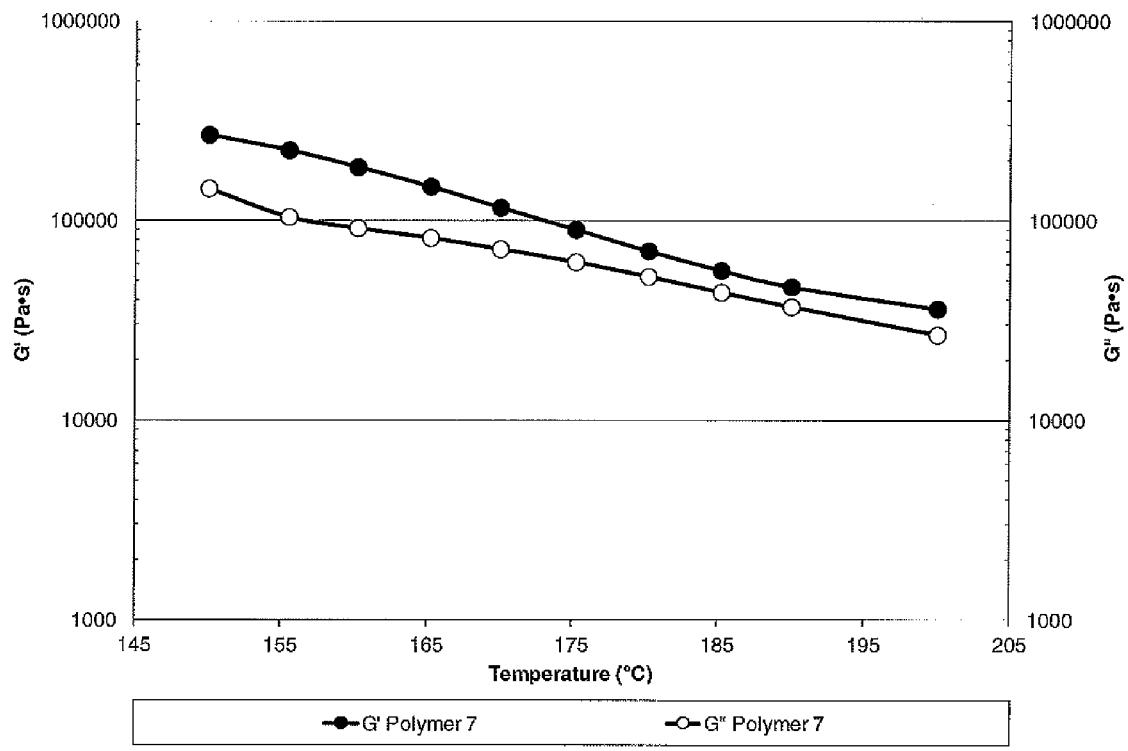
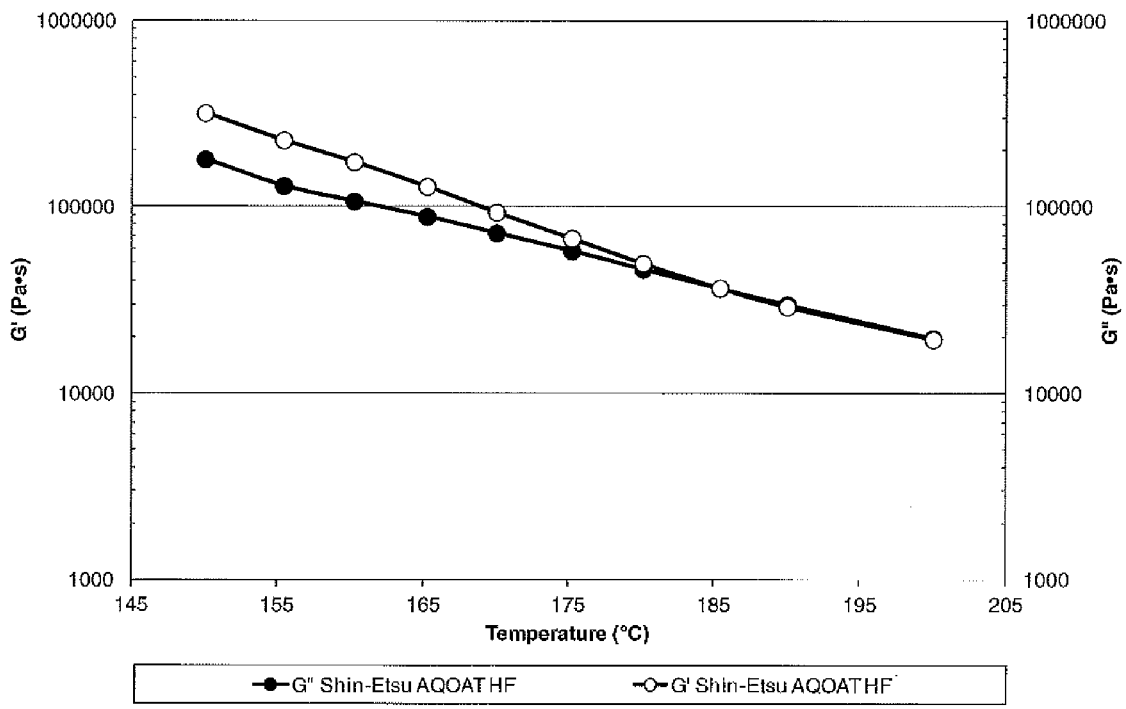

* free acetic acid, ** free succinic acid

US 9,492,550 B2

PHARMACEUTICAL COMPOSITIONS WITH ENHANCED PERFORMANCE AND IMPROVED PROCESSABILITY

CROSS REFERENCE TO RELATED APPLICATIONS

The present application claims the benefit under 35 U.S.C. 119 (e) of U.S. Provisional Patent Application Ser. No. 61/771,291, filed Mar. 1, 2013, the entire content of which is hereby expressly incorporated herein by reference.

BACKGROUND OF THE INVENTION

1. Field of the Disclosed and Claimed Inventive Concepts

The presently disclosed and claimed inventive concept(s) relates generally to hydroxypropyl methyl cellulose acetate succinate (HPMC-AS) polymers with unique substitution patterns, methods of making the polymers, and drug compositions comprising the polymers and low-performance drugs. The drug compositions have enhanced performance and/or improved process ability.

2. Background and Applicable Aspects of the Presently Disclosed and Claimed Inventive Concept(s)

Pharmaceutical compositions often include polymers to achieve specific desired therapeutic effects, including for use as coating agents, as film-formers, as rate-controlling polymers for sustained or controlled release, as stabilizing agents, as suspending agents, as tablet binders, and as viscosity-increasing agents.

HPMC-AS was originally developed as an enteric polymer for pharmaceutical dosage forms and for providing halation-preventing layers on photographic films. Enteric polymers are those that remain intact in the acidic environment of the stomach; dosage forms coated with such polymers protect the drug from inactivation or degradation in the acidic environment or prevent irritation of the stomach by the drug. HPMC-AS is currently commercially available from Shin-Etsu Chemical (Tokyo, Japan), known by the trade name "AQOAT."

Shin-Etsu manufactures three grades of AQOAT that have different combinations of substituent levels to provide enteric protection at various pH levels. The AS-LF and AS-LG grades (the "F" standing for fine and the "G" standing for granular) provide enteric protection up to a pH of about 5.5. The AS-MF and AS-MG grades provide enteric protection up to a pH of about 6.0, while the AS-HF and AS-HG grades provide enteric protection up to a pH of about 6.8. Shin-Etsu gives the following specifications for these three grades of AQOAT polymers:

| Composition of Shin-Etsu's AQOAT Polymers (wt %) | | | |
|---|---|---|---|
| Substituent | L Grades | M Grades | H Grades |
| Methoxyl Content | 20.0-24.0 | 21.0-25.0 | 22.0-26.0 |
| Hydroxypropoxyl Content | 5.0-9.0 | 5.0-9.0 | 6.0-10.0 |
| Acetyl Content | 5.0-9.0 | 7.0-11.0 | 10.0-14.0 |
| Succinoyl Content | 14.0-18.0 | 10.0-14.0 | 4.0-8.0 |

While pharmaceutical formulations of low-solubility drugs and HPMC-AS have proven effective, the AQOAT polymers manufactured by Shin-Etsu provide only a limited selection of properties for forming such formulations. There is a need to adjust the properties of polymers used in pharmaceutical compositions for numerous applications, including concentration-enhancement and controlled release applications.

BRIEF DESCRIPTION OF THE FIGURES

FIG. 1 is a plot showing the dynamic viscosity Eta* versus the angular frequency for H Grade HPMC-AS samples of Shin-Etsu AQOAT HF, Polymer 1, Polymer 3, and Polymer 7.

FIG. 2 is a plot showing the dynamic viscosity Eta* versus the temperature for H Grade HPMC-AS samples of Shin-Etsu AQOAT HF, Polymer 1, Polymer 3, and Polymer 7.

FIG. 7 is a plot showing the dynamic viscosity Eta* versus the angular frequency for H Grade HPMC-AS samples of Shin-Etsu AQOAT HF, Polymer 13 and Polymer 16.

FIG. 8 is a plot showing the dynamic viscosity Eta* versus the temperature for H Grade HPMC-AS samples of Shin-Etsu AQOAT HF, Polymer 13 and Polymer 16.

FIG. 11 is a plot showing the dynamic viscosity Eta* versus the angular frequency for L Grade HPMC-AS samples of Shin-Etsu AQOAT LF, Polymer 18 and Polymer 19.

FIG. 12 is a plot showing the dynamic viscosity Eta* versus temperature for L Grade HPMC-AS samples of Shin-Etsu AQOAT LF, Polymer 18 and Polymer 19.

FIG. 15 is a plot showing G' and G" moduli versus the temperature for Polymer 7.

FIG. 16 is a plot showing G' and G" moduli versus the temperature for Shin-Etsu AQOAT HF.

DETAILED DESCRIPTION

Figure 3:
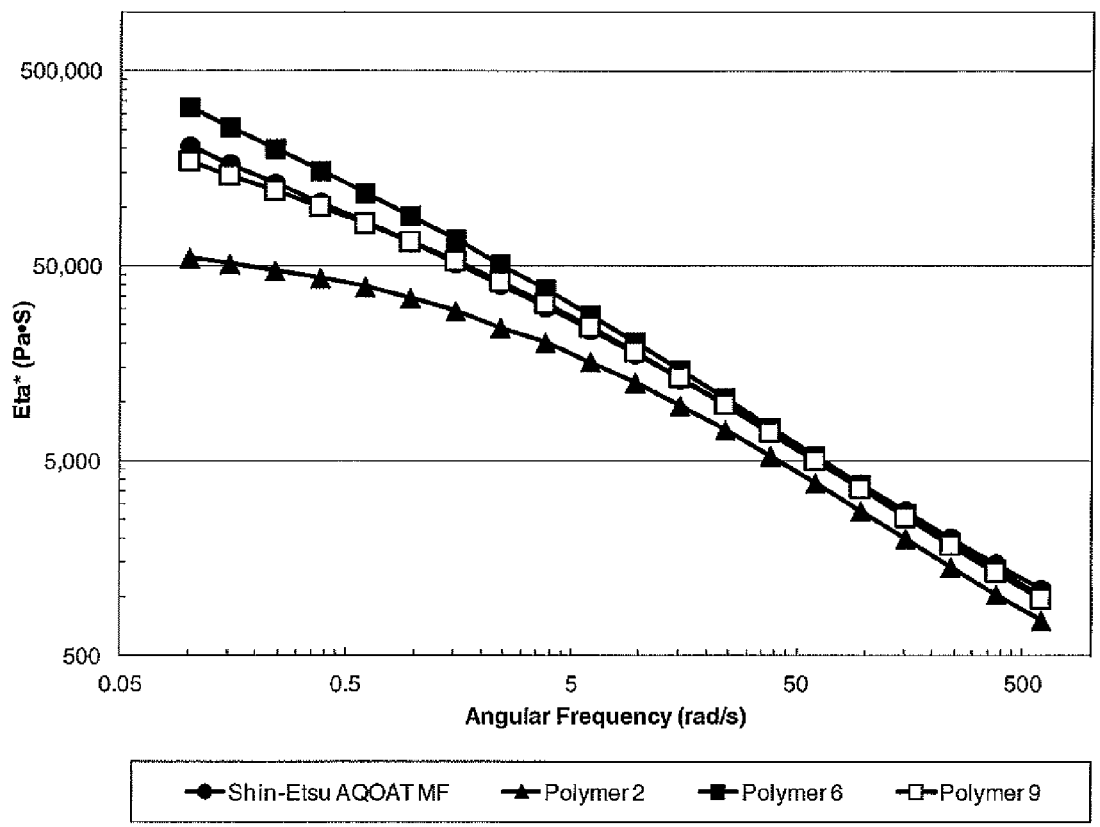
FIG. 3 is a plot showing the dynamic viscosity Eta* versus the angular frequency for M Grade HPMC-AS samples of Shin-Etsu AQOAT MF, Polymer 2, Polymer 6, and Polymer 9.

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of chemistry described herein are those well-known and commonly used in the art. Reactions and purification techniques are performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analysis, pharmaceutical preparation, formulation, and delivery, and treatment of patients.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, and/or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The presently disclosed and claimed inventive concept(s) relates generally to hydroxypropyl methyl cellulose acetate succinate (HPMC-AS) polymers with unique substitution patterns, methods of making the polymers, and drug compositions comprising the polymers and low-performance drugs. The drug compositions have enhanced performance and/or improved processability.

HPMC-AS is a substituted cellulosic polymer. By "substituted cellulosic polymer" is meant a cellulose polymer that has been modified by reaction of at least a portion of the hydroxyl groups on the saccharide repeat units with a compound to form an ester-linked and/or an ether-linked substituent.

As used herein and in the claims, by "HPMC-AS" is meant a cellulosic polymer comprising 2-hydroxypropoxy groups (—OCH$_2$CH(CH$_3$)OH), methoxy groups (—OCH$_3$), acetyl groups (—COCH$_3$), and succinoyl groups (—COCH$_2$CH$_2$COOH). Other substituents can be included on the polymer in small amounts, provided they do not materially affect the performance and properties of the HPMC-AS.

The amount of any one substituent on the polymer is characterized by its degree of substitution on the polymer. By "degree of substitution" of a substituent and/or group on the polymer is meant the average number of that substituent that is substituted on the saccharide repeat unit on the cellulose chain. The substituent may be attached directly to the saccharide repeat unit by substitution of any of the three hydroxyls on the saccharide repeat unit as shown below (C2-OH, C3-OH and C6-OH), or they may be attached through a hydroxypropoxy substituent, the hydroxypropoxy substituent being attached to the saccharide repeat unit by substitution of any of the three hydroxyls on the saccharide repeat unit as shown below (CHP—OH).

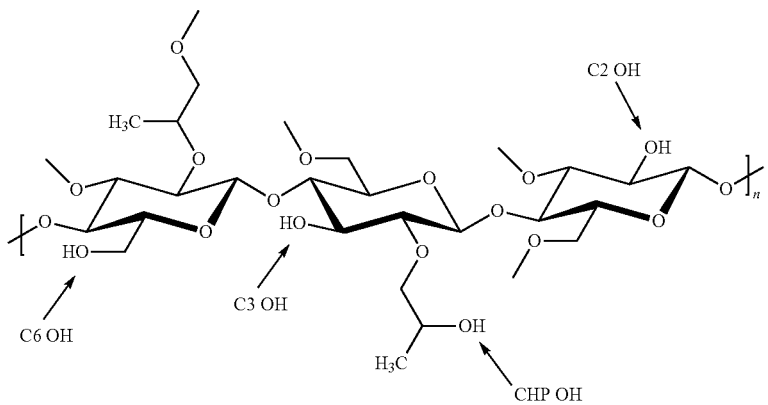

The terms related to the substitutions as used herein and throughout are defined as follows:

$DS_{Ac}$=The degree of substitution (DS) of acetyl per anhydrous glucose unit (AGU)

$DS_{Suc}$=The degree of substitution (DS) of succinoyl per anhydrous glucose unit (AGU)

$C_{HP}$=The hydroxyl group on the hydroxypropoxy (HP) side chain of HPMC or HPMC-AS $C_2$=The hydroxyl group on carbon two (2) of the cellulose backbone of HPMC or HPMC-AS $C_3$=The hydroxyl group on carbon three (3) of the cellulose backbone of HPMC or HPMC-AS $C_6$=The hydroxyl group on carbon six (6) of the cellulose backbone of HPMC or HPMC-AS $C_{HP}\,DS_{Ac}$=The DS of acetyl on the $C_{HP}$ position of HPMC-AS $C_2\,DS_{Ac}$=The DS of acetyl on the $C_2$ position of HPMC-AS $C_3\,DS_{Ac}$=The DS of acetyl on the $C_3$ position of HPMC-AS $C_6\,DS_{Ac}$=The DS of acetyl on the $C_6$ position of HPMC-AS $C_{HP}\,DS_{Suc}$=The DS of succinoyl on the $C_{HP}$ position of HPMC-AS $C_2\,DS_{Suc}$=The DS of succinoyl on the $C_2$ position of HPMC-AS $C_3\,DS_{Suc}$=The DS of succinoyl on the $C_3$ position of HPMC-AS $C_6\,DS_{Suc}$=The DS of succinoyl on the $C_6$ position of HPMC-AS % $C_6\,DS_{Ac}$=The percentage of the total acetyl DS located at the $C_6$ position % $C_3\,DS_{Ac}$=The percentage of the total acetyl DS located at the $C_3$ position % $C_6\,DS_{Suc}$=The percentage of the total succinoyl DS located at the $C_6$ % $C_3\,DS_{Suc}$=The percentage of the total succinoyl DS located at the $C_3$ position The weight percentage of acetyl and succinoyl groups on the different substitution positions can be determined by $^{13}$C-NMR analysis and calculated according to the following formula:

$$\% \, C_6 DS_{Ac} = [C_6 DS_{Ac}/(C_6 DS_{Ac} + C_3 DS_{Ac} + C_2 DS_{Ac} + C_{HP} DS_{Ac})] \times 100$$

$$\% \, C_3 DS_{Ac} = [C_3 DS_{Ac}/(C_6 DS_{Ac} + C_3 DS_{Ac} + C_2 DS_{Ac} + C_{HP} DS_{Ac})] \times 100$$

$$\% \, C_6 DS_{Suc} = [C_6 DS_{Suc}/(C_6 DS_{Suc} + C_3 DS_{Suc} + C_2 DS_{Suc} + C_{HP} DS_{Suc})] \times 100$$

$$\% \, C_3 DS_{Suc} = [C_3 DS_{Suc}/(C_6 DS_{Suc} + C_3 DS_{Suc} + C_2 DS_{Suc} + C_{HP} DS_{Suc})] \times 100$$

It has been found that the positional substitution of succinoyl and/or acetyl group per anhydrous glucose unit (AGU) is important for enhancing the performance of drugs, for example, but not by way of limitation, solubility of low soluble or insoluble drugs, and/or for improving processability of drugs. Specifically, it has been found that substitutions of succinoyl and/or acetyl on C3-OH and C6—OH are important for drug enhancement and/or processability.

The prior art HPMC-AS polymers supplied by Shin-Etsu have the following typical degree of substitution of succinoyl and/or acetyl on C3-OH and C6-OH positions, where the ranges given here are included for L, H and M Grades obtained from Shin-Etsu.

|  | Shin-Etsu L, H and M Grades |
| --- | --- |
| % $C_6\,DS_{Ac}$ | 26%-32% |
| % $C_6\,DS_{Suc}$ | 12%-18% |
| % $C_3\,DS_{Ac}$ | 27%-37% |
| % $C_3\,DS_{Suc}$ | 38%-53% |

A composition for enhancing a drug performance and improving processability of the presently disclosed and claimed inventive concept(s) comprises a polymer and the drug. The polymer comprises HPMC-AS with different degrees of substitution of succinoyl and/or acetyl groups at C6-OH and C3-OH positions. The polymer can be made from Method B.

In Method B, acetic anhydride and sodium acetate react with hydroxypropyl methyl cellulose to form an intermediate at a temperature in a range from about 85 to about 115° C. In one non-limiting embodiment, the temperature can be varied in a range of about 95 to about 115° C. In another non-limiting embodiment, the temperature can be varied in a range of about 95 to about 110° C. When the internal temperature has reached the above temperature range, the reaction mixture is stirred for a certain period of time, for example, but not by way of limitation, about 30 minutes to about 2.5 h. Then succinic anhydride is added and the mixture is stirred at the same temperature range for a time period of about 2.5 to about 23.5 hours. In one non-limiting embodiment, the time period can be varied in a range of about 2.5 to about 15.5 hours. In another non-limiting embodiment, the time period can be varied from about 2.5 to about 5.5 hours. The reaction mixture is then cooled to ambient temperature, and mixed with water to precipitate an off-white solid. The precipitate is mixed and washed with water and dried at about 65° C. using a fluidized bed dryer.

The HPMC-AS polymers prepared from Method B show different degrees of substitution of succinoyl and acetyl groups on the C6-OH and the C3-OH positions from the samples of Shin-Etsu. In one non-limiting embodiment, the percentage of the total DS of succinoyl is less than 12% at the C6-OH position (% $C_6$ $DS_{Suc}$<12%) and greater than 53% at the C3-OH position (% $C_3$ $DS_{Suc}$>53%). The percentage of the total DS of acetyl is greater than 32% at the C6-OH position (% $C_6$ $DS_{Ac}$>32%).

In another non-limiting embodiment, the percentage of the total DS of succinoyl is less than 12% at the C6-OH position (% $C_6$ $DS_{Suc}$<12%) and greater than 53% at the C3-OH position (% $C_3$ $DS_{Suc}$>53%). The percentage of the total DS of acetyl is greater than 32% at the C6-OH position (% $C_6$ $DS_{Ac}$>32%) and less than 27% at the C3-OH position (% $C_3$ $DS_{Ac}$<27%).

In yet another non-limiting embodiment, the percentage of the total DS of succinoyl is less than 10% at the C6-OH position (% $C_6$ $DS_{Suc}$<10%) and greater than 57% at the C3-OH position (% $C_3$ $DS_{Suc}$>57%). The percentage of the total DS of acetyl is from 33% to 51% at the C6-OH position (33%<% $C_6$ $DS_{Ac}$<51%) and from 16% to 20% at the C3-OH position (16%<% $C_3$ $DS_{Ac}$<20%).

In yet another non-limiting embodiment, the percentage of the total DS of succinoyl is less than or equal to 6% at the C6-OH position (% $C_6$ $DS_{Suc}$≤6%) and from 58% to 84% at the C3-OH position (58%<% $C_3$ $DS_{Suc}$<84%). The percentage of the total DS of acetyl is from 33% to 51% at the C6-OH position (33%<% $C_6$ $DS_{Ac}$<51%) and from 16% to 20% at the C3-OH position (16%<% $C_3$ $DS_{Ac}$<20%).

It has been also found that a polymer comprises HPMC-AS prepared from Method C can also improve a drug performance. In Method C, succinic anhydride and sodium acetate react with hydroxylpropyl methylcellulose to form an intermediate at a temperature in a range from about 85 to about 115° C. In one non-limiting embodiment, the temperature can be varied in a range of about 95 to about 115° C. In another non-limiting embodiment, the temperature can be varied in a range of about 95 to about 110° C. When the internal temperature has reached the above temperature range, the reaction mixture is stirred for a certain period of time, for example, but not by way of limitation, about 30 minutes to about 2.5 hours. Then acetic anhydride is added and the mixture is stirred at the same temperature range for a time period of about 2.5 to about 23.5 hours. In one non-limiting embodiment, the time period can be varied in a range of about 2.5 to about 15.5 hours. In another non-limiting embodiment, the time period can be varied from about 2.5 to about 5.5 hours. The reaction mixture is then cooled to ambient temperature, and mixed with water to precipitate an off-white solid. The precipitate is mixed and washed with water and dried at about 65° C. using a fluidized bed dryer.

The HPMC-AS polymers made from Method C also show different degrees of substitution of succinoyl and/or acetyl groups on C6-OH and C3-OH positions from the samples of Shin-Etsu. In one non-limiting embodiment, the percentage of the total DS of succinoyl is greater than 18% at the C6-OH position (% $C_6$ $DS_{Suc}$>18%) and less than 38% at the C3-OH position on the HPMC-AS (% $C_3$ $DS_{Suc}$<38%). The percentage of the total DS of acetyl is less than 26% at the C6-OH position (% $C_6$ $DS_{Ac}$<26%) and greater than 36% at the C3-OH position (% $C_3$ $DS_{Ac}$>36%).

In another non-limiting embodiment, the percentage of the total DS of succinoyl is greater than 25% at the C6-OH position (% $C_6$ $DS_{Suc}$>25%) and less than 36% at the C3-OH position (% $C_3$ $DS_{Suc}$<36%). The percentage of the total DS of acetyl is less than 24% at the C6-OH position (% $C_6$ $DS_{Ac}$<24%) and from 38% to 48% at the C3-OH position (38%<% $C_3$ $DS_{Ac}$<48%).

In yet another non-limiting embodiment, the percentage of the total DS of succinoyl is from 35% to 45% at the C6-OH position (35%<% $C_6$ $DS_{Suc}$<45%) and from 30% to 35% at the C3-OH position (30%<% $C_3$ $DS_{Suc}$<35%). The percentage of the total DS of acetyl is from 16% to 20% at the C6-OH position (16%<% $C_6$ $DS_{Ac}$<20%) and from 38% to 48% at the C3-OH position (38%<% $C_3$ $DS_{Ac}$<48%).

The term "drug" is conventional, denoting a compound having beneficial prophylactic and/or therapeutic properties when administered to an animal, especially humans. In one non-limiting embodiment, the drug is a "low-solubility drug," meaning that the drug has a minimum aqueous solubility at physiologically relevant pH (e.g., pH 1-8) of about 0.5 mg/mL or less. The presently disclosed and claimed inventive concept(s) finds greater utility as the aqueous solubility of the drug decreases. Thus, compositions of the presently disclosed and claimed inventive concept(s) are used for low-solubility drugs having an aqueous solubility of less than about 0.2 mg/mL. In one non-limiting embodiment, the low-solubility drugs have an aqueous solubility of less than about 0.1 mg/mL. In another non-limiting embodiment, the low-solubility drugs have an aqueous solubility of less than about 0.05 mg/mL. In yet another non-limiting embodiment, the low-solubility drugs having an aqueous solubility of less than about 0.01 mg/mL.

In general, it may be said that the drug has a dose-to-aqueous solubility ratio greater than about 10 mL, and more typically greater than about 100 mL, where the aqueous solubility (mg/mL) is the minimum value observed in any physiologically relevant aqueous solution (e.g., those with pH values between 1 and 8) including USP simulated gastric and intestinal buffers, and dose is in mg. Thus, a dose-to-aqueous solubility ratio may be calculated by dividing the dose (in mg) by the aqueous solubility (in mg/mL).

The drug does not need to be a low-solubility drug in order to benefit from this presently disclosed and claimed inventive concept(s), although low-solubility drugs represent a preferred class for use with the presently disclosed and claimed inventive concept(s). Even a drug that nonetheless exhibits appreciable aqueous solubility in the desired environment of use can benefit from the enhanced aqueous concentration and improved bioavailability made possible by this presently disclosed and claimed inventive concept(s) if it reduces the size of the dose needed for therapeutic efficacy or increases the rate of drug absorption in cases where a rapid onset of the drug's effectiveness is desired. In such cases, the drug may have an aqueous solubility up to about 1 to 2 mg/mL, or even as high as about 20 to 40 mg/mL.

The drugs suitable for incorporation into the HPMC-AS polymer systems in the presently disclosed and claimed inventive concept(s) can include acidic, basic, zwitterionic, or neutral organic/inorganic bioactive molecules or their salts. Examples of drugs can include, but are not limited to, analgesics, anticonvulsants, anesthetics, antidiabetic agents, anti-infective agents, antineoplastics, antirheumatic agents, cardiovascular agents, central nervous system (CNS) stimulants, dopamine receptor agonists, gastrointestinal agents, psychotherapeutic agents, urinary tract agents, antihypertensives, antianxiety agents, anticlotting agents, anticonvulsants, blood glucose-lowering agents, decongestants, antihistamines, antitussives, antineoplastics, beta blockers, antiinflammatories, antipsychotic agents, cognitive enhancers, cholesterol-reducing agents, triglyceride-reducing agents, anti-atherosclerotic agents, antiobesity agents, autoimmune disorder agents, anti-impotence agents, antibacterial and antifungal agents, hypnotic agents, anti-Parkinsonism agents, anti-Alzheimer's disease agents, antibiotics, antidepressants, antiviral agents, glycogen phosphorylase inhibitors, and cholesteryl ester transfer protein inhibitors.

Each named drug should be understood to include any pharmaceutically acceptable forms of the drug. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrugs.

Specific examples of antihypertensives can include prazosin, nifedipine, amlodipine besylate, trimazosin and doxazosin; specific examples of a blood glucose-lowering agent can include glipizide and chlorpropamide; a specific example of an anti-impotence agent is sildenafil and sildenafil citrate; specific examples of antineoplastics can include chlorambucil, lomustine and echinomycin; a specific example of an imidazole-type antineoplastic is tubulazole; a specific example of an anti-hypercholesterolemic is atorvastatin calcium; specific examples of anxiolytics can include hydroxyzine hydrochloride and doxepin hydrochloride; specific examples of anti-inflammatory agents can include betamethasone, prednisolone, aspirin, piroxicam, valdecoxib, carprofen, celecoxib, flurbiprofen and (+)—N-{4-[3-(4-fluorophenoxy)phenoxy]-2-cyclopenten-1-yl}-N-hyroxyurea; a specific example of a barbiturate is phenobarbital; specific examples of antivirals can include acyclovir, nelfinavir, delayerdine, and virazole; specific examples of vitamins/nutritional agents can include retinol and vitamin E; specific examples of beta blockers can include timolol and nadolol; a specific example of an emetic is apomorphine; specific examples of a diuretic can include chlorthalidone and spironolactone; a specific example of an anticoagulant is dicumarol; specific examples of cardiotonics can include digoxin and digitoxin; specific examples of androgens can include 17-methyltestosterone and testosterone; a specific example of a mineral corticoid is desoxycorticosterone; a specific example of a steroidal hypnotic/anesthetic is alfaxalone; specific examples of anabolic agents can include fluoxymesterone and methanstenolone; specific examples of antidepression agents can include sulpiride, [3,6-dimethyl-2-(2,4,6-trimethyl-phenoxy)-pyridin-4-yl]-(1-ethylpropyl)-a-mine, 3,5-dimethyl-4-(3'-pentoxy)-2-(2',4',6'-trimethylphenoxy)pyridine, pyroxidine, fluoxetine, paroxetine, venlafaxine and sertraline; specific examples of antibiotics can include carbenicillin indanylsodium, bacampicillin hydrochloride, troleandomycin, doxycyline hyclate, ampicillin and penicillin G; specific examples of anti-infectives can include benzalkonium chloride and chlorhexidine; specific examples of coronary vasodilators can include nitroglycerin and mioflazine; a specific example of a hypnotic is etomidate; specific examples of carbonic anhydrase inhibitors can include acetazolamide and chlorzolamide; specific examples of antifungals can include econazole, terconazole, fluconazole, voriconazole, and griseofulvin; a specific example of an antiprotozoal is metronidazole; specific examples of anthelmintic agents can include thiabendazole and oxfendazole and morantel; specific examples of antihistamines can include astemizole, levocabastine, cetirizine, levocetirizine, decarboethoxylor-atadine and cinnarizine; specific examples of antipsychotics can include ziprasidone, olanzepine, thiothixene hydrochloride, fluspirilene, risperidone and penfluridole; specific examples of gastrointestinal agents can include loperamide and cisapride; specific examples of serotonin antagonists can include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents can are THA and donepezil; a specific example of an anti-ulcer agent/H2 antagonist is famotidine; specific examples of sedative/hypnotic agents can include chlordiazepoxide and triazolam; a specific example of a vasodilator is alprostadil; a specific example of a platelet inhibitor is prostacyclin; specific examples of ACE inhibitor/antihypertensive agents can include enalaprilic acid, quinapril and lisinopril; specific examples of tetracycline antibiotics can include oxytetracycline and minocycline; specific examples of macrolide antibiotics can include erythromycin, clarithromycin, and spiramycin; a specific example of an azalide antibiotic is azithromycin; specific examples of glycogen phosphorylase inhibitors can include [R—(R*S*)]-5-chloro-N-[2-hydroxy-3-{methoxymethyl-amino}-3-oxo-1-(phenylme-thyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-o-xypropyl]amide; and specific examples of cholesteryl ester transfer protein (CETP) inhibitors include 2R,4S]-4-[(3,5-bis-trifluoromethyl-benzyl)-methoxycarbo-nyl-amino]-2-ethyl-6-trifluoromethyl-3,4-dihydro-2H-quinoline-1-carboxylic acid ethyl ester also known as torcetrapib.

CETP inhibitors, in particular torcetrapib, and methods for preparing such compounds are disclosed in detail in U.S. Pat. Nos. 6,197,786 and 6,313,142, in PCT Application Nos. WO 01/40190A1, WO 02/088085A2, and WO 02/088069A2, the disclosures of which are herein incorporated by reference. Torcetrapib has an unusually low solubility in aqueous environments such as the lumenal fluid of the human GI tract. The aqueous solubility of torcetrapib is less than about 0.04 m/ml. Torcetrapib must be presented to the GI tract in a solubility-improved form in order to achieve a sufficient drug concentration in the GI tract in order to achieve sufficient absorption into the blood to elicit the desired therapeutic effect. CETP inhibitors are also described in U.S. Pat. No. 6,723,752, which includes a number of CETP inhibitors including (2R)-3-{[3-(4-Chloro-3-ethyl-phenoxy)-phenyl]-[[3-(1,1,2,2-tetrafluoro-et-hoxy)-phenyl]-methyl]-amino}-1,1,1-trifluoro-2-propanol. Moreover, CETP inhibitors included herein are also described in U.S. patent application Ser. No. 10/807,838 filed Mar. 23, 2004, and U.S. Patent Application No. 60/612,863, filed Sep. 23, 2004, which includes (2R,4R,4aS)-4-[Amino-(3,5-bis-(trifluoromethyl-phenyl)-methyl]-2-ethyl-6-(trifluorom-ethyl)-3,4-dihydroquinoline-1-carboxylic acid isopropyl ester. Further CETP inhibitors can include JTT-705, also known as S-[2-([[1-(2-ethylbutyl)cyclohexyl]carbonyl] amino)phenyl]2-methylpropanet-hioate, and those compounds disclosed in PCT Application No. WO04/020393, such as S-[2-([[1-(2-ethylbutyl)cyclohexyl]carbonyl]amino) phenyl]2-methyl-propanethioate, trans-4-[[[2-[[[[3,5-bis(tri-fluoromethyl)phenyl]methyl](2-methyl-2H-tetra-zol-5-yl) amino]methyl]-4-(trifluoromethyl)phenyl]ethylamino] methyl]cycloh-exaneacetic acid and trans-4-[[[2-[[[[3,5-bis (trifluoromethyl)phenyl]methyl](2-methyl-2H-tetra-zol-5-yl)amino]methyl]-5-methyl-4-(trifluoromethyl)phenyl] ethylamino]methyl-1]cyclohexaneacetic acid, the drugs disclosed in commonly owned U.S. patent application Ser. Nos. 09/918,127 and 10/066,091, the disclosures of both of which are incorporated herein by reference, and the drugs disclosed in the following patents and published applications, the disclosures of all of which are incorporated herein by reference: DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; WO 9835937 A1; JP 11049743; WO 0018721; WO 0018723; WO 0018724; WO 0017164; WO 0017165; WO 0017166; WO 04020393; EP 992496; and EP 987251.

Representative examples of other drugs suitable for use in the presently disclosed and claimed inventive concept(s) can include, but are not limited to, itraconazole, ezetimibe, albuterol sulfate, amoxicillin, bupropion hydrochloride, carbidopa, cefaclor, diclofenac sodium, erythromycin, loratidine, lithium carbonate, methyl phenidate, metaprolol tartrate, nifedipine, omeprazole, sotalol hydrochloride, verapamil hydrochloride albuterol sulfate, amoxicillin, bupropion hydrochloride, carbidopa, cefaclor, diclofenac sodium, erythromycin, felodipine, loratidine, lithium carbonate, methyl phenidate, metaprolol tartrate, nifedipine, omeprazole, sotalol hydrochloride, verapamil hydrochloride or a therapeutically relevant combination thereof. The above list of drugs is not intended to be exhaustive.

In contrast to conventional wisdom, the relative degree of enhancement in aqueous concentration and bioavailability provided by the compositions of the presently disclosed and claimed inventive concept(s) can generally improve for drugs as solubility decreases and hydrophobicity increases. In fact, the inventors have recognized a subclass of hydrophobic drugs that are essentially aqueous insoluble, highly hydrophobic, and are characterized by a set of physical properties. This subclass, referred to herein as "hydrophobic drugs," exhibits dramatic enhancements in aqueous concentration and bioavailability when formulated using the polymers of the presently disclosed and claimed inventive concept(s). In addition, compositions of hydrophobic drugs and the polymers of the presently disclosed and claimed inventive concept(s) may also have improved physical stability relative to commercial grades of polymer.

The first property of hydrophobic drugs is that they are very hydrophobic. By very hydrophobic is meant that the Log P value of the drug may have a value of at least 4.0, a value of at least 5.0, and even a value of at least 5.5. Log P, defined as the base 10 logarithm of the ratio of (1) the drug concentration in an octanol phase to (2) the drug concentration in a water phase when the two phases are in equilibrium with each other, is a widely accepted measure of hydrophobicity. Log P may be measured experimentally or calculated using methods known in the art. When using a calculated value for Log P, the highest value calculated using any generally accepted method for calculating Log P is used. Calculated Log P values are often referred to by the calculation method, such as C log P, A log. P, and M log P. The Log P may also be estimated using fragmentation methods, such as Crippen's fragmentation method (J. Chem. Inf. Comput. Sci. 27, 21-35 (1987)); Viswanadhan's fragmentation method (J. Chem. Inf. Comput. Sci. 29, 163-172 (1989)); or Broto's fragmentation method (Eur. J. Med. Chem.-Chim. Theor. 19, 71 (1984)). Preferably the Log P value is calculated by using the average value estimated using Crippen's, Viswanadhan's, and Broto's fragmentation methods.

The second property of hydrophobic drugs is that they have a low solubility parameter. The calculation of the solubility parameter is disclosed in U.S. Pat. No. 8,207,232, the entirety of which is hereby expressly incorporated herein by reference. The solubility parameter may be about 22 $(J/cm^3)^{1/2}$ or less, about 21.5 $(J/cm^3)^{1/2}$ or less, and even about 21 $(J/cm^3)^{1/2}$ or less.

Primarily as a consequence of these properties, hydrophobic drugs typically have a very low aqueous solubility. By very low aqueous solubility is meant that the minimum aqueous solubility at physiologically relevant pH (pH of 1 to 8) is less than about 100 µg/ml and often less than about 10 µg/ml. In addition, hydrophobic drugs often have a very high dose-to-solubility ratio. Very low aqueous solubility often leads to poor or slow absorption of the drug from the fluid of the gastrointestinal tract, when the drug is dosed orally in a conventional manner. For very low solubility drugs, poor absorption generally becomes progressively more difficult as the dose (mass of drug given orally) increases. Thus, a second property of hydrophobic drugs is a very high dose (in mg) to solubility (in mg/ml) ratio (ml). By "very high dose-to-solubility ratio" is meant that the dose-to-solubility ratio may have a value of at least 1000 ml, at least 5,000 ml, or even at least 10,000 ml.

Hydrophobic drugs also typically have very low absolute bioavailabilities. Specifically, the absolute bioavailability of drugs in this subclass when dosed orally in their unformulated state (i.e., drug alone) is less than about 10% and more often less than about 5%.

In one non-limiting embodiment of the presently disclosed and claimed inventive concept(s), the drug can be an acid-sensitive drug, meaning that the drug either chemically reacts with or otherwise degrades in the presence of acidic species. Acid-sensitive drugs often include functional groups that are reactive under acidic conditions, such as sulfonyl ureas, hydroxamic acids, hydroxy amides, carbamates, acetals, hydroxy ureas, esters, and amides. Drugs that include such functional groups may be prone to reactions such as hydrolysis, lactonization, or transesterification in the presence of acidic species.

Specific examples of acid-sensitive drugs are set forth below, by way of example only. Each named drug should be understood to include the neutral form of the drug, pharmaceutically acceptable salts, and prodrugs. Examples of acid-sensitive drugs can include, but are not limited to, quinoxaline-2-carboxylic acid [4(R)-carbamoyl-1(S)-3-fluorobenzyl-2(S), 7-dihydroxy-7-methyl-octyl]amide-; quinoxaline-2-carboxylic acid [1-benzyl-4-(4,4-difluoro-cyclohexyl)-2-hydroxy-4-hydroxycarbamoyl-butyl]-amide; quinoxaline-2-carboxylic acid [1-benzyl-4-(4,4-difluoro-1-hydroxy-cyclohexyl)-2-hydroxy-4-hydroxycarbam-oyl-butyl]-amide; (+)-N-{3-[3-(4-fluorophenoxy)phenyl]-2-cyclopenten-1-yl}-N-hydroxyurea; omeprazole; etoposide; famotidine; erythromycin; quinapril; lansoprazole; and progabide.

It is known in the pharmaceutical arts that low-solubility drugs often show poor bioavailability or irregular absorption, the degree of irregularity being affected by factors such as dose level, fed state of the patient, and form of the drug.

With the increasing number of poorly water-soluble compounds in contemporary drug discovery pipelines, the concept of supersaturation as a tool for enhancing bioavailability has been used, especially in the field of oral drug delivery where increased intraluminal concentrations through supersaturation are expected to enhance the intestinal absorption. For this enhanced intestinal absorption to take place, supersaturation must be induced and maintained in the gastrointestinal environment. Upon induction, the thermodynamically unstable state of supersaturation has to be maintained for a time period long enough to allow intestinal absorption. Maintenance of the supersaturated state is very important.

It has been found that inclusion of excipients that delay precipitation may stabilize supersaturation in vitro. Pharmaceutical excipients used for this purpose can include polymer, surfactants and cyclodextrins. The excipients are usually named as anti-nucleation agents. HPMC-AS in the presently disclosed and claimed inventive concept(s) can be used as an anti-nucleation agent to promote and maintain drug supersaturation for a poorly soluble compound.

It is well-known that oral absorption of a drug depends upon the drug's solubility in the gastrointestinal (GI) milieu and upon its GI wall permeability. When dissolution testing is used to forecast the in vivo performance of a drug, it is critical that the in vivo test mimic the conditions in vivo as close as possible. It has been observed that biorelevant media can provide a more accurate simulation on pharmacokinetic profiles than simulated gastric fluid or simulated intestinal fluid. The biorelevant medium used in the presently disclosed and claimed inventive concept(s) is SIF® powder, a Fast State Simulated Intestinal Fluid (FaSSIF) phosphate buffer, available from Phares Drug Delivery AG, Baselland, Switzerland.

Supersaturation can be investigated using solvent-shift method. In this method, a water bath at 37° C. with a dissolution vessel can be used. The size of the dissolution vessel depends on the test volume. A HPMC-AS polymer and a biorelevant medium can be added to form a mixture into the vessel and equilibrated at 37° C. The mixture is constantly stirred using any known stirring equipment in the art. Supersaturated solution of a drug is prepared and added into the vessel. Samples can be taken at various time points and centrifuged. The drug concentrations can be analyzed using any known analysis technology, for example, but not by way of limitation, HPLC analysis with UV detection.

Melt flow index (MFI) is a measure of the ease of flow of the melt of a thermoplastic polymer. It is defined as the mass of polymer, in grams, flowing in ten minutes through a capillary of a specific diameter and length by a pressure applied via prescribed alternative gravimetric weights for alternative prescribed temperatures.

The melt flow indices of the polymers can be measured according to ASTM D 1238 at the conditions specified for the given polymer type. Such standard methods specify the geometry and other constraints on the device used as well as the combinations of conditions. The device is essentially an upright, narrow cylindrical barrel fitted with a plunger and a removable (for cleaning) orifice at the bottom. The barrel is temperature controlled and a defined weight is placed on the plunger to provide the prescribed force and thus pressure on the plunger, which drives the polymer melt through the orifice. Typically, polymer pellets are loaded into the barrel and allowed to come to the measurement temperature, well above the polymer melting point, then the weight is applied to the plunger, forcing polymer through the orifice. The extrudate is measured via literal weighing or by volumetric methods (plunger travel) using known melt density.

A tablet is a pharmaceutical dosage form. It comprises a mixture of active substances and excipients, usually in powder form, pressed or compacted from a powder into a solid dose. The excipients can include diluents, binders or granulating agents, glidants (flow aids) and lubricants to ensure efficient tabletting; disintegrants to promote tablet break-up in the digestive tract; sweeteners or flavors to enhance taste; and pigments to make the tablets visually attractive. A wide variety of binders may be used, some common ones including lactose, dibasic calcium phosphate, sucrose, corn (maize) starch, microcrystalline cellulose, povidone polyvinylpyrrolidone and modified cellulose (for example, but not by way of limitation, hydroxypropyl methylcellulose and hydroxyethylcellulose).

Often, an ingredient is also needed to act as a disintegrant to aid tablet dispersion once swallowed, releasing the active pharmaceutical ingredient (API) for absorption. Some binders, such as starch and cellulose, are also excellent disintegrants. Stearic acid can be used as a flow aid and lubricant. The HPMC-AS polymers in the presently disclosed and claimed inventive concept(s) are made as tablets and their harnesses are measured.

In the tablet-pressing process, it is important that all ingredients be fairly dry, powdered or granular, somewhat uniform in particle size, and freely flowing. Mixed particle sized powders can segregate during manufacturing operations due to different densities, which can result in tablets with poor drug or API content uniformity but granulation should prevent this. Content uniformity ensures that the same API dose is delivered with each tablet.

To make a tablet, powder can be fed into a horizontal feeder from a powder hopper. The powder floods a portion of a die table and a die. The desired fill volume, called tablet weight, can be adjusted with the first control, called the weight cam. After the excess powder has been scraped off, the powder in the die can be pressed together by the action of the upper and lower punches rolling over the pressure rolls. The desired tablet thickness is obtained by moving the lower pressure roll either away from or closer to the fixed upper pressure roll. Compressing force or compression force is a function of a combination of any set of unique fill volumes (weight) and thickness values that one might choose for any particular active ingredient and tablet size/shape.

Measuring tablet hardness (breaking force) plays a vital role in defining dosage form with optimum physical characteristics and testing whether produced dosage form meets the defined specifications in manufacturing. Testing tablet hardness is more than ensuring the mechanical integrity of produced tablets during subsequent processes. Because the hardness of a tablet directly relates to all other physical parameters, it is a fast and efficient test that indicates whether specifications such as disintegration time and friability will be met. It is therefore essential, that hardness measurement is done correctly—and that the equipment used to test tablet hardness guarantees repeatable results.

Herein the term "hardness" is actually used as a synonym for breaking force or resistance to crushing strength. In simple terms, tablet hardness is the force (load) required to break a tablet. The standard method used for tablet hardness testing is compression testing. The tablet is placed between two jaws that frus the tablet. The machine measures the force applied to the tablet and detects when it fractures. In the presently disclosed and claimed inventive concept(s), the compressing force is measure as kilo Newton (KN) and hardness is measured as kilopond (kp).

Solid dispersion is an approach to disperse a poorly soluble drug in a polymer matrix in solid state. The drug can exist in amorphous or micro crystalline form in the mixture, which provides a fast dissolution rate and/or apparent solubility in the gastric and intestinal fluids. Several techniques have been developed to prepare solid dispersions, including co-precipitation (see, e.g., U.S. Pat. Nos. 5,985,326 and 6,350,786), fusion, spray-drying (see, e.g., U.S. Pat. No. 7,008,640), and hot-melt extrusion (see, e.g., U.S. Pat. No.

7,081,255). All these techniques provide a highly dispersed drug molecule in a polymer matrix, usually at the molecular level or in a microcrystalline phase.

Solid dispersions of a drug in a matrix can be prepared by forming a homogeneous solution or melt of the drug and matrix material followed by solidifying the mixture by cooling or removal of solvent. Such solid dispersions of crystalline drugs often show enhanced bioavailability when administered orally relative to oral compositions comprising undispersed crystalline drug.

A spray dried solid dispersion of a sparingly-soluble drug in HPMC-AS of the presently disclosed and claimed inventive concept(s) can have unique properties making it broadly useful for preparing oral dosage forms. While not wishing to be bound by any particular theory or mechanism, it is believed that in order for a solid amorphous dispersion of a drug in a matrix material to function optimally in improving the bioavailability of sparingly-soluble drugs, the matrix material must generally provide the following functions: 1. disperse the drug, thereby preventing or retarding the rate of crystallization in the solid state, 2. dissolve in vivo, thereby allowing the drug to be released to the gastrointestinal tract, 3. inhibit the precipitation or crystallization of aqueous dissolved drug.

If a drug does not have a strong tendency to crystallize from the amorphous solid state, then only the latter two functions are required. When a solid amorphous dispersion of a drug in HPMC-AS is prepared, the drug can, either prior to or following dissolution of the drug HPMC-AS dispersion, reach a concentration substantially higher than the equilibrium solubility of the drug alone. That is, the drug reaches a supersaturated concentration, and this supersaturated concentration will be maintained for a relatively long time period.

A HPMC-AS polymer in the presently disclosed and claimed inventive concept(s) functions well in all three respects noted above such that it is unique among known matrix materials in its ability to inhibit the precipitation or crystallization of a broad range of sparingly soluble drugs from a supersaturated solution further, and again without wishing to be bound by theory, it is believed that spray drying affects rapid solvent removal so that crystallization of drug and the HPMC-AS polymer can largely be prevented, or at least minimized relative to other methods of forming dispersions, including other solvent removal processes such as rotary evaporation. In addition, in many cases spray drying affects removal of solvent sufficiently fast that even phase separation of amorphous drug and the HPMC-AS polymer can largely be prevented or minimized. Thus, a HPMC-AS polymer in the presently disclosed and claimed inventive concept(s) and spray drying can afford a better, more truly homogeneous dispersion in which the drug is more efficiently dispersed in the polymer. Increased efficiency of dispersion from spray drying gives, relative to other methods of making dispersions, a higher drug concentration in in vitro tests.

Although the key ingredients present in the solid amorphous compositions of the presently disclosed and claimed inventive concept(s) are simply the drug to be delivered and HPMC-AS, the inclusion of other excipients in the dispersion may be useful. For example, but not by way of limitation, polymers other than HPMC-AS that are soluble in aqueous solutions over at least a portion of the range pH 1.0 and 8.0 can be included in the dispersion along with HPMC-AS. Examples of other polymers can include, but are not limited to, polyvinylpyrrolidone (PVP), hydroxypropyl cellulose (HPC), or HPMC. HPMC-AS may have as its primary benefit inhibition of the precipitation or crystallization of drug from supersaturated solution regarding that the drug is crystalline or amorphous. In one non-limiting embodiment, a drug, HPMC-AS, and one or more additional polymers can be co-spray dried, wherein the drug and HPMC-AS can constitute no more than about 75% of the dispersion.

Another type of excipient useful as a component of the dispersions herein is a surface-active agent such as a fatty acid and alkyl sulfonate. Such materials can advantageously be employed to increase the rate of dissolution by facilitating wetting, thereby increasing the maximum drug concentration and the degree of supersaturation attained, and also to inhibit crystallization or precipitation of drug by interacting with dissolved drug by mechanisms such as complexation, formation of inclusion complexes, formation of micelles or adsorbing to the surface of solid drug, crystalline or amorphous. These surface active agents may comprise up to about 25% of the spray-dried dispersion.

Addition of pH modifiers such as acids, bases, or buffers can also be beneficial. pH modifiers can advantageously serve to retard the dissolution of the dispersion (e.g., acids such as citric acid or succinic acid) or, alternatively, to enhance the rate of dissolution of the dispersion (e.g., bases such as sodium acetate or amines). Addition of conventional matrix materials, surface active agents, fillers, disintegrants, or binders may be added as part of the dispersion itself, added by granulation via wet or mechanical or other means. When such additives are included as part of the dispersion itself, they can be mixed with drug and HPMC-AS in the spray drying solvent, and may or may not dissolve along with the drug and HPMC-AS prior to forming the dispersion by spray drying. These materials may comprise up to about 25% of the drug/HPMC-AS/additive dispersion.

In addition to drug and HPMC-AS (and other polymers as discussed immediately above), other conventional formulation excipients can be employed in the compositions of this presently disclosed and claimed inventive concept(s), including those excipients well known in the art. Generally, excipients such as fillers, disintegrating agents, pigments, binders, lubricants, flavorants, and so forth can be used for customary purposes and in typical amounts without affecting the properties of the compositions. These excipients are utilized after the HPMC-AS/drug dispersion has been formed, in order to formulate the dispersion into tablets, capsules, suspensions, powders for suspension, creams, transdermal patches, and the like.

The term spray-drying is used conventionally and broadly refers to processes involving breaking up liquid mixtures into small droplets (atomization) and rapidly removing solvent from the mixture in a container (spray-drying apparatus) where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This is accomplished by either (1) maintaining the pressure in the spray-drying apparatus at a partial vacuum (e.g., 0.01 to 0.50 atm); (2) mixing the liquid droplets with a warm drying gas; or (3) both. For example, but not by way of limitation, a solution of drug and HPMC-AS in acetone can be suitably spray-dried by spraying the solution at a temperature of about 50° C. into a chamber held at about 0.01 to about 0.2 atm total pressure by connecting the outlet to a vacuum pump. Alternatively, the acetone solution can be sprayed into a chamber where it is mixed with nitrogen or other inert gas at a temperature of about 80° C. to about 180° C. and a pressure of about 1.0 to about 1.2 atm.

Generally, the temperature and flow rate of the drying gas can be chosen so that the HPMC-AS/drug-solution droplets are dry enough by the time they reach the wall of the apparatus that they are essentially solid, so that they form a fine powder and do not stick to the apparatus wall. The actual length of time to achieve this level of dryness depends on the size of the droplets. Droplet sizes generally range from about 1 μm to about 500 μm in diameter, with about 5 to about 100 μm being more typical. The large surface-to-volume ratio of the droplets and the large driving force for evaporation of solvent leads to actual drying times of a few seconds or less. This rapid drying is critical to the particles maintaining a uniform, homogeneous composition instead of separating into drug-rich and polymer-rich phases.

Such dispersions which have a homogeneous composition can be considered solid solutions and may be supersaturated in drug. Such homogeneous dispersions are preferred in that the maximum supersaturated concentration (MSSC) value obtained when a large amount of drug is dosed can be higher for such dispersions relative to dispersions for which at least a portion of the drug is present as a drug-rich amorphous or crystalline phase. Solidification time can be less than about 20 seconds. In one non-limiting embodiment, the solidification time can be less than about 5 seconds. In another non-limiting embodiment, the solidification time can be less than about 2 seconds. In general, to achieve this rapid solidification of the drug/polymer solution, the sizes of droplets formed during the spray drying process are less than about 100 μm in diameter. In one non-limiting embodiment, the sizes of droplets are less than about 50 μm in diameter. In another non-limiting embodiment, the sizes of droplets are less than about 25 μm in diameter. The resultant solid particles thus formed are generally less than about 100 μm in diameter. In one non-limiting embodiment, the resultant solid particles are less than about 50 μm in diameter. In another non-limiting embodiment, the resultant solid particles are less than about 25 μm in diameter.

Following solidification, the solid powder may stay in the spray-drying chamber for about 5 to about 50 seconds, further evaporating solvent from the solid powder. The final solvent content of the solid dispersion as it exits the dryer can be low, since this reduces the mobility of drug molecules in the dispersion, thereby improving its stability. Generally, the residual solvent content of the dispersion can be less than about 10 wt %. In one non-limiting embodiment, the residual solvent content of the dispersion can be less than about 2 wt %.

The dispersions can then be post-processed to prepare them for administration using methods known in the art such as roller compaction, fluid bed agglomeration, or spray coating.

Spray-drying processes and spray-drying equipment are described generally in Perry's Chemical Engineers' Handbook, Sixth Edition (R. H. Perry, D. W. Green, J. O. Maloney, eds.) McGraw-Hill Book Co. 1984, page 20-54 to 20-57 and "Atomization and Spray-Drying," Chem. Eng. Prog. Monograph. Series, 50 (1954) No. 2), the entirety of which are hereby expressly incorporated herein by reference.

The solution spray-dried to form the HPMC-AS/drug dispersion can contain only drug and HPMC-AS in a solvent. Typically, the ratio of drug to HPMC-AS in the solution ranges from about 1:0.2 to about 1:100. In one non-limiting embodiment, the ratio of drug to HPMC-AS ranges from about 1:0.4 to about 1:20. The minimum drug:polymer ratio that yields satisfactory results can vary from drug to drug and is best determined in the in vitro dissolution tests.

Essentially, solvents suitable for spray-drying can be any organic compound in which the drug and HPMC-AS are mutually soluble. In one non-limiting embodiment, the solvent is also volatile with a boiling point of 150° C. or less. Examples of solvents can include, but are not limited to alcohols such as methanol, ethanol, n-propanol, iso-propanol and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Lower volatility solvents such as dimethyl acetamide or dimethylsulfoxide can also be used. Mixtures of solvents can also be used, as can mixtures with water as long as the polymer and HPMC-AS are sufficiently soluble to make the spray-drying process practical.

Spray-dried solutions and the resulting dispersions can also contain various additives that aid in the stability, dissolution, tableting, or processing of the dispersion. As mentioned previously, examples of such additives can include, but are not limited to, surfactants, pH-controlling substances (e.g., acids, bases, and buffers), fillers, disintegrants, or binders. Such additives can be added directly to the spray-drying solution such that the additive is dissolved or suspended in the solution as slurry. Alternatively, such additives can be added following the spray-drying process to aid in forming the final dosage form.

Hot-melt extrusion (HME) is a widely used method of preparation for amorphous solid dispersion. As used herein, hot melt extrusion is the process of mixing two or more components using high shear mixing and controlled temperature capability of the extruder. The hot melt extruder consists of four primary parts: motor that controls the rotation of the screws, the screws (primary source of shear and moving the material), the barrels that house the screws and provide temperature control and the die (the exit port) that controls the shape and size of the extrudates. The powder material (either granular or in powder form) is generally fed into the extruder feeding port at controlled rate while the extruder screws are rotating. The material is then conveyed forward using the rotation of screw and the friction of the material against the barrel surface. Depending on the type of extruder, a single screw or a twin screw may be used to operate either in counter or co-rotating mode. The screws can be appropriately designed to achieve required degree of mixing. In general the barrels are segmented to enable the temperature adjustment in each zone throughout the screw length. The exit port (the die system) controls the shape and size of the extrudates.

The extrudate is then cooled and either shaped by calendaring or pelletized and milled to a desired particle size. The final milled extrudate is then typically blended with additional excipients and compressed. The extrusion process will be performed at temperatures above the Tg of the polymer and high enough for the API to either melt and/or dissolve into the polymer matrix.

HME can provide the opportunity to produce sophisticated multi-layer and multi-functional composites by creating and bringing together several melt streams in a single fully integrated manufacturing process. Thus, one or more active drug substances can be dispersed in one or more polymeric matrices.

A solution of drug and HPMC-AS can be prepared in a solvent such as acetone. The acetone solution is dropped into acidified water to co-precipitate the drug/polymer mixture. The precipitate is then separated by filtration and washed by the acidified water, followed by drying. The dried powder is screened to obtain uniform size particles. The powder mixture is then fed through a hot melt extruder with the heating barrels being set at about 70-140° C. to obtain extrudate rods. The extrudate rods are then cooled to room temperature and milled by mechanical milling methods.

The following examples illustrate the presently disclosed and claimed inventive concept(s), parts and percentages being by weight, unless otherwise indicated. Each example is provided by way of explanation of the presently disclosed and claimed inventive concept(s), not limitation of the presently disclosed and claimed inventive concept(s). In fact, it will be apparent to those skilled in the art that various modifications and variations can be made in the presently disclosed and claimed inventive concept(s) without departing from the scope or spirit of the invention. For instance, features illustrated or described as part of one embodiment, can be used on another embodiment to yield a still further embodiment. Thus, it is intended that the presently disclosed and claimed inventive concept(s) covers such modifications and variations as come within the scope of the appended claims and their equivalents.

EXAMPLES

Method for Measuring Distribution of Positional Substituents in HPMC-AS

As described previously, acetate and succinate can be substituted on HPMC to form HPMC-AS. For each substituent, there are four possible positions or sites to substitute, i.e. directly on to cellulose ring C2, C3, and/or C6 positions as well as end-cap terminal OH of hydroxypropoxy chain. $^{13}C$ NMR spectroscopy can be used to determine positional substitution of both acetate and succinate on anhydroglucose ring. Determination of substituent distribution in cellulose ether using a $^{13}C$ NMR is described in detail in Makromol. Chem., Vol. 191, 681-691 (1990), and Macromolecues, Vol. 20, 2413-2418 (1987), the entirety of which are hereby expressly incorporated herein by reference.

Figure 17:
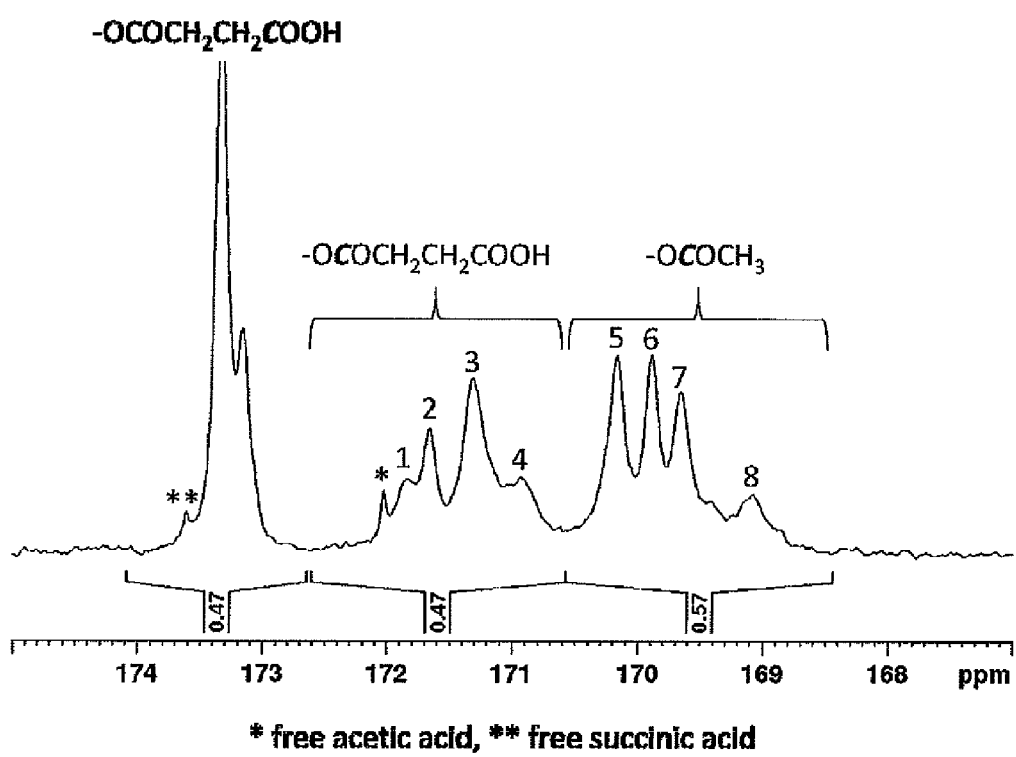
FIG. 17 is a partial $^{13}$C NMR Spectrum of HPMC-AS in DMSO-d6.

All NMR spectra for HPMC-AS samples were acquired using Broker AVM 500 MHz NMR spectrometer equipped with a 10 mm BBO z-gradient probe. The HPMC-AS samples were dissolved in DMSO-$d_6$. The carbonyl region of the spectrum (168.0-174.0 ppm) indicated the peaks of both acetyl CO and succinoyl CO carbons as shown in FIG. 17. For succinoyl substitution, two sets of peaks were observed due to acid and ester carbonyl carbons. Ester carbonyl carbons from acetate and succinate substitutions showed unique peak(s) depending on the positions of substituents on anhydroglucose ring and hydroxypropoxy chain. Assignments of peaks were based on literature values, model compound and 2D NMR analysis.

| Peak # | Assignment | Chemical shift (ppm) |
|---|---|---|
| 1 | Succinoyl bound to C6 | 171.80 |
| 2 | Succinoyl bound to HP | 171.65 |
| 3 | Succinoyl bound to C3 | 171.30 |
| 4 | Succinoyl bound to C2 | 170.90 |
| 5 | Acetyl bound to C6 | 170.15 |
| 6 | Acetyl bound to HP | 169.85 |
| 7 | Acetyl bound to C3 | 169.65 |
| 8 | Acetyl bound to C2 | 169.10 |

For area estimation, the peaks were deconvoluted and the estimated areas were normalized with DS of acetyl and succinoyl which were obtained from the methods described below.

Determination of Free Acids, and Acetyl and Succinoyl Contents—USP 34-NF 29 Hypromellose Acetate Succinate NF Monograph Free acids, acetyl and succinoyl contents were determined according to the methods described in United States Pharmacopeia National Formulary 2011: USP 34-NF 29 Hypromellose Acetate Succinate NF Monograph.

1. Limit of Free Acetic and Succinic Acids

Phosphoric acid solution—1.0 mL of 1.25 M phosphoric acid was transferred into a 50-mL volumetric flask, and diluted with water to volume.

0.02 M Phosphate buffer—5.44 g of monobasic potassium phosphate was dissolved in 2 L of water.

Diluent—0.02 M Phosphate buffer with 1 N sodium hydroxide was adjusted to a pH of 7.5.

Acetic acid stock solution—Approximately 20 mL of water was added to a stoppered, 100-mL volumetric flask. The flask was placed on a balance, and tared. 2.0 mL of the glacial acetic acid was transferred to the flask, and the weight of the acid added was recorded. The flask was filled with water to volume. 6.0 mL of this solution was transferred into a 100-mL volumetric flask, and diluted with water to volume.

Succinic acid stock solution—About 130 mg of succinic acid was added into a 100-mL volumetric flask. About 50 mL of water was added, and the contents were swirled until the succinic acid was fully dissolved. The flask was filled with water to volume.

Mobile phase—0.02 M Phosphate buffer was adjusted to a pH of 2.8 by the dropwise addition of 6 M phosphoric acid and passed through a 0.22-µm nylon filter.

Standard solution—4.0 mL of the Acetic acid stock solution was transferred into a 25-mL volumetric flask. 4.0 mL of the succinic acid stock solution was transferred into the same flask, diluted with Mobile phase to volume, and mixed. The solution was prepared in duplicate.

Test solution—4.0 mL of diluent was transferred into a glass vial containing about 102 mg HPMC-AS, and the contents were stirred for about 2 hours. Then, 4.0 mL of the phosphoric acid solution was transferred into the same vial to bring the pH of the Test solution to about 3 or less. The vial was inverted several times to ensure complete mixing, centrifuge, and the clear supernatant was used as the Test solution.

Chromatographic system (USP 34 Chromatography <621>)—The liquid chromatography was equipped with a 215-nm detector and a 4.6-mm×15-cm column that contained 5-µm packing L1 (i.e. Restek UltraAqueous C18, 5 µm, 150×4.6 mm, Cat. #9178565-700). The column temperature was maintained at about 30° C. The flow rate was about 1 mL per minute, and the run time was about 15 minutes. The Standard solution was analyzed, and the peak responses were recorded as directed for Procedure: the column efficiency, determined from the succinic acid peak, was not less than 8000 theoretical plates; the tailing factor of this peak was between 0.9 and 1.5; and the relative S, in standard deviation for six replicate injections was not more than 2.0% for each peak. The duplicate Standard solution was analyzed, and the peak responses were recorded as directed for Procedure. After each run sequence, the column was flushed first by about 50% water and about 50% acetonitrile for about 60 minutes and then by 100% methanol for about 60 minutes. The column was stored in 100% methanol.

Procedure—Equal volumes (10 μl) of the Standard solution and the Test solution were separately injected into the chromatograph, the chromatogram was recorded, and the peak areas were measured corresponding to acetic and succinic acids. The percentage of free acetic acid was calculated, in the portion of HPMC-AS by the formula:

$$0.0768(W_A/W)(r_{UA}/r_{SA})$$

where $W_A$ is the weight of glacial acetic acid, in mg, used to prepare the Acetic acid stock solution; W is the weight of HPMC-AS, in mg, used to prepare the Test solution; and $r_{UA}$ and $r_{SA}$ are the peak responses for acetic acid obtained from the Test solution and the Standard solution, respectively. The percentage of free succinic acid, $S_{free}$, was calculated in the portion of HPMC-AS by the formula:

$$1.28(W_S/W)(r_{US}/r_{SS})$$

where $W_S$ is the weight of succinic acid, in mg, used to prepare the Succinic acid stock solution; $r_{US}$ and $r_{SS}$ are the peak responses for succinic acid obtained from the Test solution and the Standard solution, respectively; and W is as defined above.

2. Contents of Acetyl and Succinoyl Groups

Phosphoric acid solution, Acetic acid stock solution, Succinic acid stock solution, Mobile phase, Standard solution, and Chromatographic system—proceed as directed in the test for Limit of free acetic and succinic acids.

Test solution—4.0 mL of 1.0 N sodium hydroxide was transferred into a glass vial having about 12.4 mg of HPMC-AS. The solution was stirred for 4 hours. Then, 4.0 mL of 1.25 M phosphoric acid was added into the same vial to bring the pH of the solution to about 3 or less. The test sample solution vial was inverted several times to ensure complete mixing, and passed through a 0.22-μm filter. The clear filtrate was used as the Test solution.

Procedure—Equal volumes (10 μL) of the Standard solution and the Test solution were separately injected into the chromatograph, the chromatograms was recorded, and the peak areas corresponding to acetic and succinic acids were measured. The percentage of acetic acid, A, was calculated in the portion of HPMC-AS by the formula:

$$0.0768(W_A/W_U)(r_{UA}/r_{SA})$$

where $W_A$ is the weight of acetic acid, in mg, used to prepare the Acetic acid stock solution; $W_U$ is the weight of HPMC-AS, in mg, used to prepare the Test solution; and $r_{UA}$ and $r_{SA}$ are the peak responses for acetic acid obtained from the Test solution and the Standard solution, respectively. The percentage of acetyl groups (—COCH$_3$) was calculated in the portion of Hydroxypropyl Methylcellulose Acetate Succinate taken by the formula:

$$0.717(A-A_{free})$$

where $A_{free}$ is the percentage of free acetic acid, as determined in the test for Limit of free acetic and succinic acids; and A is as defined above. The percentage of succinic acid was calculated in the portion of HPMC-AS by the formula:

$$1.28(W_S/W_U)(r_{US}/r_{SS})$$

where $W_S$ is the weight of succinic acid, in mg, used to prepare the Succinic acid stock solution; $W_U$ is as defined above; and $r_{US}$ and $r_{SS}$ are the peak responses for succinic acid obtained from the Test solution and the Standard solution, respectively.

The percentage of succinoyl groups (—COC$_2$H$_4$COOH) was calculated in the portion of HPMC-AS by the formula:

$$0.856(S-S_{free})$$

where S is as defined above; and $S_{free}$ is the percentage of free succinic acid, as determined in the test for Limit of free acetic and succinic acids.

Determination of Hydroxypropoxy and Methoxy Contents—USP 34-NF 29 Hypromellose USP Monograph Hydroxypropoxy and methoxy contents were determined according to the methods described in United States Pharmacopeia National Formulary 2011: USP 34-NF 29 Hypromellose USP Monograph.

1. Procedure

Apparatus—For the reaction vial, a 5-mL pressure-tight serum vial, 50 mm in height, 20 mm in outside diameter, and 13 mm in inside diameter at the mouth was used. The vial was equipped with a pressure-tight septum having a polytetrafluoroethylene-faced butyl rubber and an airtight seal using an aluminum crimp or any sealing system that provided sufficient airtightness. A heater having a heating module that had a square-shape aluminum block with holes 20 mm in diameter and 32 mm in depth was used, into which the reaction vial was fit. The heating module was also equipped with a magnetic stirrer capable of mixing the contents of the vial, or a reciprocal shaker that performed a reciprocating motion of about 100 times/min was used.

Hydriodic acid—A reagent having a typical concentration of HI of about 57% was used.

Internal standard solution—30 mg/mL of n-octane in o-xylene

Standard solution—2.0 mL of Hydriodic acid and 2.0 mL of Internal standard solution were added into a suitable serum vial containing about 60 and 100 mg of adipic acid. The vial was closed securely with a suitable septum stopper and weighed. About 15 mL and 22 mL of isopropyl iodide were added through the septum with a syringe. The vial was weighed again, and the weight of isopropyl iodide added was calculated, by difference. 45 mL of methyl iodide was added and weighed again. The weight of methyl iodide added was calculated, by difference. The reaction vial was shaken well, and the layers were allowed to separate. The upper layer was used as the Standard solution.

Sample solution—0.065 g of dried HPMC-AS was transferred to a 5-mL thick-walled reaction vial equipped with a pressure tight septum-type closure. About 60 and 100 mg of adipic acid were added and 2.0 mL of Internal standard solution was pipette into the vial. 2.0 mL of Hydriodic acid was pipetted into the mixture, immediately the vial was capped tightly, and weighed. Using the magnetic stirrer equipped in the heating module, or using a reciprocal shaker, contents of the vial was mixed continuously. The contents were heated and maintained at the temperature of about 130±2° for about 60 min. The vial was shaken well by hand at 5-min intervals during the initial 30 min of the heating time if a reciprocal shaker or magnetic stirrer could not be used. The vial was allowed to cool, and weighed.

2. Chromatographic System

Mode—GC

Detector—Thermal conductivity or hydrogen flame ionization

Column—3- to 4-mm×1.8- to 3-m glass column packed with 20% liquid phase G28 on 100- to 120-mesh support S1C that is not silanized Column temperature—100° C.

Carrier gas—Helium with the thermal conductivity detector was used; helium or nitrogen was used for the hydrogen flame-ionization detector.

Flow rate—With the Standard solution; the flow rate was adjusted so that the retention time of the internal standard was about 10 min.

Injection size—1-2 mL

3. Analysis

Samples—Upper layer of the Standard solution and the Sample solution

The percentage of —$OCH_3$ was calculated in the portion of HPMC-AS by:

$$\text{Result} = 21.864 \times (R_{Ua}/R_{Sa}) \times (W_{Sa}/W_U)$$

$R_{Ua}$=peak area ratio of methyl iodide to n-octane from the Sample solution $R_{Sa}$=peak area ratio of methyl iodide to n-octane from the Standard solution $W_{Sa}$=weight of methyl iodide in the Standard solution (mg)

$W_U$=weight of HPMC-AS, calculated on the dried basis, taken for the Sample solution (mg)

The percentage of —$OC_3H_6OH$ was calculated in the portion of HPMC-AS by:

$$\text{Result} = 44.17 \times (R_{Ub}/R_{Sb}) \times (W_{Sb}/W_U)$$

$R_{Ub}$=peak area ratio of isopropyl iodide to n-octane from the Sample solution $R_{Sb}$=peak area ratio of isopropyl iodide to n-octane from the Standard solution $W_{Sb}$=weight of isopropyl iodide in the Standard solution (mg)

$W_U$=weight of HPMC-AS, calculated on the dried basis, taken for the Sample solution (mg)

Determination of Molecular Weight (MW) Distribution by Size-Exclusion Chromatography (SEC)

Molecular weight is the sum of the atomic weights of the atoms in a molecule. As used herein with respect to polymers, the terms molecular weight, average molecular weight, mean molecular weight, and apparent molecular weight refer to the arithmetic mean of the molecular weight of individual macromolecules as measured by size-exclusion chromatography (SEC).

The relative molecular weight averages from the analytical SEC were calculated versus poly(ethylene glycol/ethylene oxide) (PEG/PEO) standards with narrow molecular weight distribution.

1. Chromatography Set-Up

All Waters modules in the set-up are manufactured by Waters Corporation, 34 Maple Street, Milford, Mass. 01757, USA. The set-up was replaced with similar from different manufacturer(s).

Waters M515 solvent delivery system
Waters M717 autosampler
Waters M2414 differential refractive index detector (DRI) for the relative SEC**
Column bank(s)—see the details in the "Analysis conditions" section below Waters Empower 2 software
* RI range 1.00 to 1.75 RIU
Measurement range $7 \times 10^{-7}$ RIU
Drift—$2 \times 10^{-7}$ RIU 2. Analysis Conditions for SEC Mobile Phase—55% 0.1 M Lithium Acetate/45% Ethanol
Flow Rate—0.8 ml/min
Columns—TSKgel guard (6 mm×40 mm)+2 Linear TSK GMPWx1 columns.; 13 um; 300 mm×7.8 mm (TOSOH Bioscience LLC, 3604 Horizon Drive, Suite 100, King of Prussia, Pa. 19406, USA
Column Temperature—35° C.
DRI (differential refractive index) Detector Temperature—35° C.

Calibration—PEO/PEG standards with narrow molecular weight distribution (PSS-USA, Inc. Amherst Fields Research Park, 160 Old Farm Road, Amherst, Mass. 01002)
Sample Concentration—Typically 1 mg/ml (unless otherwise noted)
Injection volume—200 μl Glass Transition Temperature Measurement The glass transition temperature, $T_g$, is the temperature at which an amorphous solid, such as glass or a polymer, becomes brittle or strong on cooling, or soft or pliable on heating. $T_g$ can be determined, for example, by differential scanning calorimetry (DSC). DSC measures the difference in the amount of heat required to raise temperature of a sample and a reference as a function of temperature. During the phase transition, such as a change from an amorphous state to a crystalline state, the amount of heat required changes. For a solid that has virtually no crystalline components, a single glass transition temperature indicates that the solid is a molecular dispersion.

The glass transition (Tg) measurement was conducted using TA Instruments Q2000 DSC. Approximately 5 mg of sample was loaded to the standard aluminum pan. A heat-cool-heat temperature ramp measurement was conducted with a temperature range from about −20° C. to 190° C. and a heating and cooling rate of about 20° C./min. The glass transition temperature was reported through the second heat data and it was measured based on the half-height of the heat flow curve.

Viscosity Measurement 4.3 g of sodium hydroxide was dissolved in carbon dioxide free water to make 1000 mL of a sodium hydroxide solution. Sodium hydroxide solution was added to 2.00 g of HPMC-AS, previously dried, to make 100.0 g. A stopper was inserted into the vessel, and the contents were dissolved by constant shaking for about 30 minutes. The temperature of the solution was adjusted to 20±0.1° C. The viscosity was determined in an ubbelohde viscometer or equivalent, as directed by USP 34 NF29—Procedure for Cellulose Derivative under Viscosity under Viscosity <911>, the entirety of which is hereby expressly incorporated herein by reference. These measurements can also be conducted using a Cannon Mini-PV-x automated viscometer.

Synthesis of HPMC-AS

Comparative Example 1

Synthesis for HPMC-AS at 115° C. (Method A)

Acetic acid was added to an oven-dried 1 L glass reactor containing a nitrogen inlet and outlet, condenser and overhead mechanical stirrer. HPMC (Benecel™ E5, available from Ashland, Inc.) was slowly added while the mixture was stirred at 200 RPM. Acetic anhydride was added and the mixture was stirred at ambient temperature for about 30 min. Succinic anhydride and sodium acetate were added successively and the mixture was stirred at 300 RPM while heating to 115° C. When the internal temperature reached 115° C., stirring was continued for about 3 h. Then the temperature was decreased. The reaction mixture was cooled down to ambient temperature, and mixed with water to precipitate an off-white solid. The precipitate was washed with additional quantities of water and dried at 65° C. using a fluidized bed dryer. Table 1 lists different HPMC-AS samples obtained with various amounts of reactants from Method A.

TABLE 1

Samples Synthesized Using Methods A

| Sample | Acetic Acid (g) | HPMC (g) | Acetic Anhydride (g) | Succinic Anhydride (g) | Sodium Acetate (g) |
|---|---|---|---|---|---|
| Polymer 1 | 400.2 | 110.0 | 98.0 | 12.0 | 55.0 |
| Polymer 8 | 400.2 | 110.1 | 57.1 | 25.1 | 110.0 |
| Polymer 9 | 400.2 | 110.1 | 85.9 | 17.9 | 55.1 |

Example 1A

Synthesis for HPMC-AS (Method B)

Acetic acid was added to an oven-dried 1 L glass reactor containing a nitrogen inlet and outlet, condenser and overhead mechanical stirrer. HPMC was slowly added while the mixture was stirred at 200 RPM. Acetic anhydride and sodium acetate were added sequentially, and the mixture was heated to 115° C. while stirring at 300 RPM. When the internal temperature reached 115° C., stirring was continued for about 30 min (Initial Hold Time). Succinic anhydride was added and the mixture was stirred at about 115° C. for about 2.5 h (Hold Time after $2^{nd}$ Addition). The reaction mixture was cooled down to ambient temperature and mixed with water to precipitate an off-white solid. The precipitate was washed with water and dried at 65° C. using a fluidized bed dryer. Polymers 2-4 and Polymer 10 obtained using various amounts of reactants are listed in Table 2A.

Example 1B

Synthesis for HPMC-AS (Method B 1)

Acetic acid was added to an oven-dried 1 L glass reactor containing a nitrogen inlet and outlet, condenser and overhead mechanical stirrer. HPMC was slowly added while the mixture was stirred at 200 RPM. Acetic anhydride and sodium acetate were added, and the mixture was heated to 115° C. while stirring at 300 RPM. When the internal temperature reached 115° C., stirring was continued for about 2 hours for Polymer 11 and about 1.0 hour for Polymer 12 in Table 2A (Initial Hold Time). Succinic anhydride was added and the mixture was stirred at about 115° C. for about 2.5 h (Hold Time after $2^{nd}$ Addition). Water was then added slowly while maintaining the reaction temperature between 45° C. and 85° C. until the water addition was complete. The reaction mixture was cooled down to ambient temperature, and mixed with water to precipitate an off-white solid. The precipitate was washed with additional quantities of water and dried at 65° C. using a fluidized bed dryer. The obtained Polymers 11-12 are listed in Table 2A.

Example 1C

Synthesis for HPMC-AS (Method B2)

Acetic acid was added to an oven-dried 1 L glass reactor containing a nitrogen inlet and outlet, condenser and overhead mechanical stirrer. HPMC was slowly added while the mixture was stirred at 200 RPM. Acetic anhydride and sodium acetate were added and the mixture was heated to 85° C. When the internal temperature reached 85° C., stirring was continued for about 1 hour (Initial Hold Time). Succinic anhydride was added and the mixture was heated at 85° C. for about 1.5 hours and then heated up to 115° C. over about 30 minutes and held at 115° C. for about 2.5 hours (Hold Time after $2^{nd}$ Addition was totally 4.5 hours). The reaction mixture was cooled down to ambient temperature and mixed with water to precipitate an off-white solid. The precipitate was washed with water and dried at 65° C. using a fluidized bed dryer. The obtained Polymer 13 is listed in Table 2A.

TABLE 2A

Samples Synthesized Using Methods B, B1 and B2

| Sample | HPMC Grade | HPMC (g) | Acetic Acid (g) | Acetic Anhydride (g) | Succinic Anhydride (g) | Sodium Acetate (g) | Initial Hold Time (h) | Hold Time After $2^{nd}$ Addition |
|---|---|---|---|---|---|---|---|---|
| Polymer 2 | E5* | 110.0 | 400.1 | 57.0 | 25.1 | 110.0 | 0.5 | 2.5 |
| Polymer 3 | E5 | 110.0 | 400.0 | 85.8 | 17.8 | 55.0 | 0.5 | 2.5 |
| Polymer 4 | E5 | 110.0 | 400.1 | 45.1 | 27.1 | 110.0 | 0.5 | 2.5 |
| Polymer 10 | E3** | 110.0 | 400.0 | 85.8 | 17.9 | 55.1 | 0.5 | 2.5 |
| Polymer 11 | E5 | 110.2 | 400.2 | 49.0 | 17.8 | 55.1 | 2.0 | 2.5 |
| Polymer 12 | E3/E5 (1:1) | 110.1 | 400.2 | 85.9 | 17.8 | 55.0 | 1.0 | 2.5 |
| Polymer 13 | E5 | 55.0 | 200.3 | 50.1 | 8.9 | 27.5 | 1.0 | 4.5 |

*E5 refers to Benecel ™ E5, available from Ashland Inc.
**E3 refers to Benecel ™ E3, available from Ashland Inc.

Example 1D

Synthesis for HPMC-AS (Method B3)

Acetic acid was added to an oven-dried 1 L glass reactor containing a nitrogen inlet and outlet, condenser and overhead mechanical stirrer. HPMC was slowly added while the mixture was stirred at 200 RPM. Acetic anhydride and sodium acetate were added, and the mixture was stirred at 300 RPM and at ambient temperature for a period of time (Hold Time After $1^{st}$ Addition). Then the mixture was heated to 85° C. When the internal temperature reached 85° C., stirring was continued for a period of time (Initial Hold Time). Succinic anhydride was added and the mixture was stirred at about 85° C. for a period of time (Hold Time After $2^{nd}$ Addition). Water was then added slowly while maintaining the reaction temperature between 45° C. and 85° C. until the water addition was complete. The reaction mixture was cooled down to ambient temperature and mixed with water to precipitate an off-white solid. The precipitate was washed with water and dried at 65° C. using a fluidized bed dryer. Polymers 14-18 obtained using various amounts of reactants are listed in Table 2B.

Example 1F

Synthesis for HPMC-AS (Method B4)

Acetic acid was added to an oven-dried 1 L glass reactor containing a nitrogen inlet and outlet, condenser and overhead mechanical stirrer. HPMC (Benecel™ E3) was slowly added while the mixture was stirred at 200 RPM. Sodium acetate was added and the mixture was heated to 85° C. while stirring at 300 RPM. When the internal temperature reached 85° C., acetic anhydride was added and stirring was continued for a period of time (Initial Hold Time). Succinic anhydride was added and the mixture was stirred at about 85° C. for a period of time (Hold Time After $2^{nd}$ Addition). Water was then slowly added while maintaining the reaction temperature between 45° C. and 85° C. until the water addition was complete. The reaction mixture was cooled down to ambient temperature and mixed with water to precipitate an off-white solid. The precipitate was washed with water and dried at 65° C. using a fluidized bed dryer. Polymer 19 obtained is listed in Table 2B.

TABLE 3A

Samples Synthesized Using Method C

| Sample | Acetic Acid (g) | HPMC (g) | Acetic Anhydride (g) | Succinic Anhydride (g) | Sodium Acetate (g) |
|---|---|---|---|---|---|
| Polymer 5 | 400.1 | 110.0 | 57.1 | 25.0 | 110.1 |
| Polymer 6 | 400.0 | 110.0 | 85.8 | 17.9 | 55.0 |
| Polymer 7 | 400.0 | 110.1 | 98.0 | 12.1 | 110.0 |
| Polymer 20 | 400.0 | 110.0 | 85.8 | 17.9 | 110.0 |
| Polymer 21 | 400.1 | 110.0 | 90.1 | 12.1 | 110.02 |
| Polymer 22 | 400.1 | 110.0 | 80.0 | 17.0 | 110.6 |

Example 2B

Synthesis for HPMC-AS (Method C1)

Acetic acid was added to an oven-dried 1 L glass reactor containing a nitrogen inlet and outlet, condenser and overhead mechanical stirrer. HPMC was slowly added while the mixture was stirred at 200 RPM. Sodium acetate was added and the mixture was heated to 85° C. while stirring at 300 RPM. When the internal temperature reached 85° C., succinic anhydride was added and stirring was continued for a period of time (Hold Time After $1^{st}$ Addition). Acetic anhydride was added, and the mixture was stirred at about 85° C.

TABLE 2B

Samples Synthesized Using Methods B3 and B4

| Sample | HPMC Grade | HPMC (g) | Acetic Acid (g) | Acetic Anhydride (g) | Succinic Anhydride (g) | Sodium Acetate (g) | Hold Time After 1st Addition (h) | Initial Hold Time (h) | Hold Time After $2^{nd}$ Addition (h) |
|---|---|---|---|---|---|---|---|---|---|
| Polymer 14 | E3 | 110.2 | 330.0 | 90.1 | 44.0 | 55.1 | 0 | 1.0 | 4 |
| Polymer 15 | E3 | 110.7 | 400.4 | 100.2 | 35.1 | 110.2 | 0.5 | 1.0 | 2 |
| Polymer 16 | E5 | 110.1 | 400.0 | 100.0 | 35.0 | 110.0 | 0.5 | 1.0 | 2 |
| Polymer 17 | E3 | 110.0 | 400.2 | 100.0 | 35.1 | 110.1 | 0.5 | 1.0 | 2 |
| Polymer 18 | E5 | 110.0 | 400.1 | 60.1 | 50.1 | 110.0 | 0 | 1.0 | 4 |
| Polymer 19 | E3 | 110.0 | 330.0 | 60.0 | 50.1 | 55.1 | 0 | 1.0 | 4 |

Example 2A

Synthesis for HPMC-AS (Method C)

Acetic acid was added to an oven-dried 1 L glass reactor containing a nitrogen inlet and outlet, condenser and overhead mechanical stirrer. HPMC (Benecel™ E5) was slowly added while the mixture was stirred at 200 RPM. Succinic anhydride and sodium acetate were added sequentially and the mixture was heated to 115° C. while stirring at 300 RPM. When the internal temperature reached 115° C., stirring was continued for about 30 min. Acetic anhydride was added, and the mixture was stirred at about 115° C. for about 2.5 h. The reaction mixture was cooled down to ambient temperature and mixed with water to precipitate an off-white solid. The precipitate was mixed and washed with water and dried at 65° C. using a fluidized bed dryer. Polymers 5-7 and Polymers 20-22 obtained using various amounts of reactants are listed in Table 3A.

for a period of time (Hold Time after $2^{nd}$ Addition). Water was then added slowly while maintaining the reaction temperature between 45° C. and 85° C. until the water addition was complete. The reaction mixture was cooled down to ambient temperature and mixed with water to precipitate an off-white solid. The precipitate was washed with water and dried at 65° C. using a fluidized bed dryer. Polymers 23-26 obtained using various amounts of reactants are listed in Table 3B.

Example 2C

Synthesis for HPMC-AS (Method C2)

Acetic acid was added to an oven-dried 1 L glass reactor containing a nitrogen inlet and outlet, condenser and overhead mechanical stirrer. HPMC was slowly added while the mixture was stirred at 200 RPM. Sodium acetate was added and the mixture was heated to 85° C. while stirring at 300 RPM. When the internal temperature reached 85° C., succinic anhydride was added and stirring was continued for a period of time (Hold Time After $1^{st}$ Addition). Acetic anhydride (66.5 g) was added, and the mixture was stirred at about 85° C. for a period of time (Hold Time after 2$^{nd}$ Addition). A second portion of acetic anhydride (60.5 g) was added and the mixture was stirred at 85° C. for about 2.5 hours. Water was then added slowly while maintaining the reaction temperature between 45° C. and 85° C. until the water addition was complete. The reaction mixture was cooled down to ambient temperature and mixed with water to precipitate an off-white solid. The precipitate was mixed and washed with water and dried at 65° C. using a fluidized bed dryer. The obtained Polymer 27 is listed in Table 3B.

TABLE 3B

Samples Synthesized Using Methods C1 and C2

| Sample | HPMC grade | HPMC (g) | Acetic Acid (g) | Acetic Anhydride (g) | Succinic Anhydride (g) | Sodium Acetate (g) | Hold Time after 1st Addition (h) | Hold Time after 2$^{nd}$ Addition (h) |
|---|---|---|---|---|---|---|---|---|
| Polymer 23 | E3/E5 (1:1) | 82.5 | 300.3 | 262.5 | 30.0 | 108.2 | 2.5 | 3 |
| Polymer 24 | E3/E5 (1:1) | 55.0 | 200.1 | 300.0 | 10.0 | 60.0 | 2.5 | 3 |
| Polymer 25 | E3 | 110.0 | 330.1 | 299.9 | 16.0 | 110.1 | 2.0 | 3 |
| Polymer 26 | E3 | 110.0 | 400.1 | 250.1 | 22.1 | 110.1 | 3.0 | 3 |
| Polymer 27 | E3 | 110.2 | 330.2 | 127.0 | 12.0 | 110.0 | 3.0 | 2.0 |

Characterization of HPMC-AS Samples

Table 4 shows the sample characterization data. Commercial samples from Shin-Etsu, corresponding to Shin-Etsu AQOAT LF, Shin-Etsu AQOAT MF, and Shin-Etsu AQOAT HF, are included for comparison. F represents fine powder grade with average particle size of about 5 μm.

TABLE 4

Sample Characterization Data

| Sample | Acetyl wt % | Succinoyl wt % | HP wt % | Me wt % | SEC M$_w$ | Viscosity (cp) | Tg (° C.) | HPMC-AS Grade |
|---|---|---|---|---|---|---|---|---|
| Polymer 1 | 11.65 | 6.15 | 8.25 | 23.83 | 64,100 | 3.7 | 120.3 | H |
| Polymer 2 | 10.15 | 12.40 | 7.68 | 22.84 | 61,100 | 3.6 | 117.0 | M |
| Polymer 3 | 12.10 | 6.60 | 8.56 | 24.50 | 52,800 | 3.6 | 110.0 | H |
| Polymer 4 | 7.40 | 15.55 | 8.21 | 21.86 | 56,100 | 3.6 | 110.6 | L |
| Polymer 5 | 7.50 | 15.75 | 7.95 | 22.44 | 210,000 | 4.3 | 111.3 | L |
| Polymer 6 | 9.10 | 11.10 | 8.28 | 23.88 | 108,000 | 3.6 | 112.1 | M |
| Polymer 7 | 13.35 | 7.75 | 8.25 | 24.01 | 114,000 | 4.2 | 111.9 | H |
| Polymer 8 | 7.85 | 15.80 | 7.54 | 22.35 | 129,000 | 3.6 | 117.7 | L |
| Polymer 9 | 10.05 | 10.55 | 8.19 | 23.3 | 79,100 | 3.6 | 119.2 | M |
| Polymer 10 | 12.45 | 7.40 | 8.04 | 23.78 | 26,700 | 2.4 | 114.0 | H |
| Polymer 11 | 8.75 | 9.60 | 8.01 | 23.77 | 48,200 | 3.6 | 120.3 | — |
| Polymer 12 | 12.20 | 6.50 | 7.88 | 22.90 | 38,000 | 2.9 | 114.2 | H |
| Polymer 13 | 12.40 | 7.50 | 8.18 | 23.62 | 53,200 | 3.7 | 116.1 | H |
| Polymer 14 | 10.10 | 10.65 | 7.88 | 23.45 | 33,900 | 2.4 | 112.8 | M |
| Polymer 15 | 10.70 | 8.05 | 7.68 | 23.44 | 33,100 | 2.6 | 116.1 | — |
| Polymer 16 | 10.90 | 7.00 | 8.09 | 23.4 | 59,600 | 3.8 | 118.6 | H |
| Polymer 17 | 11.85 | 7.30 | 8.14 | 23.08 | 33,800 | 2.4 | 112.3 | H |
| Polymer 18 | 8.20 | 14.55 | 7.74 | 22.16 | 54,000 | 3.7 | 114.9 | L |
| Polymer 19 | 7.60 | 14.70 | 7.71 | 23.19 | 32,700 | 2.4 | 114.2 | L |
| Polymer 20 | 11.55 | 11.25 | 8.42 | 23.50 | 209,000 | 4.4 | 111.1 | — |
| Polymer 21 | 12.60 | 7.90 | 8.43 | 22.50 | 147,000 | 3.7 | 111.2 | H |
| Polymer 22 | 10.90 | 11.00 | 8.32 | 22.07 | 187,000 | 3.6 | 111.3 | M |
| Polymer 23 | 8.05 | 15.80 | 7.55 | 22.53 | 91,600 | 3.0 | 114.3 | L |
| Polymer 24 | 12.75 | 8.50 | 8.43 | 23.33 | 62,400 | 3.1 | 116.8 | — |
| Polymer 25 | 12.95 | 8.00 | 7.98 | 22.88 | 48,400 | 2.3 | 111.3 | H |
| Polymer 26 | 10.80 | 10.80 | 7.81 | 22.43 | 54,100 | 2.5 | 111.6 | M |
| Polymer 27 | 12.20 | 8.30 | 8.09 | 23.99 | 51,100 | 2.4 | 114.6 | — |
| Shin-Etsu AQOAT LF | 8.15 | 14.30 | 7.08 | 24.11 | 122,000 | 2.7 | 117.3 | L |
| Shin-Etsu AQOAT MF | 9.65 | 10.80 | 7.37 | 24.82 | 104,000 | 2.8 | 119.2 | M |
| Shin-Etsu AQOAT HF | 12.00 | 7.50 | 7.58 | 25.15 | 102,000 | 2.8 | 118.7 | H |

Table 5 shows the distributions of acetyl and succinoyl substitutions on $C_{HP}$—OH, $C_2$—OH, $C_3$—OH and $C_6$—OH of AGU, which were determined by $^{13}C$ NMR analysis. The percentage of acetyl and succinoyl at the C6 and C3 hydroxyl positions based on the data of Table 5 is shown in Table 5A.

TABLE 5

Acetyl and Succinoyl Substitution Distribution as determined by NMR analysis

| Sample | $C_{HP} DS_{Ac}$ | $C_6 DS_{Ac}$ | $C_3 DS_{Ac}$ | $C_2 DS_{Ac}$ | $C_{HP} DS_{Suc}$ | $C_6 DS_{Suc}$ | $C_3 DS_{Suc}$ | $C_2 DS_{Suc}$ |
|---|---|---|---|---|---|---|---|---|
| Polymer 1 | 0.132 | 0.182 | 0.227 | 0.130 | 0.032 | 0.027 | 0.061 | 0.030 |
| Polymer 2 | 0.127 | 0.230 | 0.145 | 0.119 | 0.034 | 0.003 | 0.243 | 0.043 |
| Polymer 3 | 0.148 | 0.233 | 0.206 | 0.127 | 0.016 | 0.000 | 0.121 | 0.029 |
| Polymer 4 | 0.081 | 0.232 | 0.074 | 0.068 | 0.079 | 0.000 | 0.238 | 0.092 |
| Polymer 5 | 0.088 | 0.074 | 0.200 | 0.102 | 0.069 | 0.149 | 0.145 | 0.054 |
| Polymer 6 | 0.127 | 0.112 | 0.199 | 0.107 | 0.033 | 0.124 | 0.084 | 0.042 |
| Polymer 7 | 0.153 | 0.151 | 0.382 | 0.123 | 0.030 | 0.072 | 0.067 | 0.032 |
| Polymer 8 | 0.095 | 0.146 | 0.166 | 0.079 | 0.074 | 0.093 | 0.204 | 0.046 |
| Polymer 9 | 0.117 | 0.171 | 0.202 | 0.112 | 0.041 | 0.064 | 0.108 | 0.056 |
| Polymer 10 | 0.158 | 0.227 | 0.196 | 0.161 | 0.020 | 0.0045 | 0.128 | 0.034 |
| Polymer 11 | 0.115 | 0.221 | 0.091 | 0.080 | 0.041 | 0.000 | 0.137 | 0.059 |
| Polymer 12 | 0.164 | 0.231 | 0.175 | 0.134 | 0.009 | 0.000 | 0.120 | 0.031 |
| Polymer 13 | 0.162 | 0.230 | 0.214 | 0.123 | 0.021 | 0.000 | 0.136 | 0.031 |
| Polymer 14 | 0.126 | 0.234 | 0.126 | 0.119 | 0.049 | 0.000 | 0.168 | 0.055 |
| Polymer 15 | 0.119 | 0.227 | 0.141 | 0.133 | 0.035 | 0.000 | 0.122 | 0.041 |
| Polymer 16 | 0.135 | 0.211 | 0.153 | 0.127 | 0.019 | 0.007 | 0.104 | 0.041 |
| Polymer 17 | 0.138 | 0.228 | 0.178 | 0.148 | 0.019 | 0.000 | 0.130 | 0.033 |
| Polymer 18 | 0.099 | 0.219 | 0.095 | 0.089 | 0.049 | 0.021 | 0.255 | 0.054 |
| Polymer 19 | 0.084 | 0.225 | 0.071 | 0.086 | 0.079 | 0.006 | 0.231 | 0.067 |
| Polymer 20 | 0.134 | 0.127 | 0.348 | 0.112 | 0.044 | 0.113 | 0.104 | 0.038 |
| Polymer 21 | 0.131 | 0.151 | 0.347 | 0.123 | 0.030 | 0.081 | 0.067 | 0.023 |
| Polymer 22 | 0.118 | 0.109 | 0.308 | 0.127 | 0.044 | 0.099 | 0.097 | 0.044 |
| Polymer 23 | 0.092 | 0.030 | 0.298 | 0.081 | 0.051 | 0.199 | 0.108 | 0.061 |
| Polymer 24 | 0.145 | 0.116 | 0.391 | 0.122 | 0.015 | 0.129 | 0.039 | 0.036 |
| Polymer 25 | 0.141 | 0.119 | 0.384 | 0.132 | 0.027 | 0.092 | 0.047 | 0.038 |
| Polymer 26 | 0.129 | 0.095 | 0.315 | 0.112 | 0.023 | 0.146 | 0.068 | 0.039 |
| Polymer 27 | 0.147 | 0.158 | 0.304 | 0.124 | 0.027 | 0.089 | 0.054 | 0.041 |
| Shin-Etsu AQOAT LF | 0.107 | 0.160 | 0.137 | 0.095 | 0.064 | 0.049 | 0.198 | 0.061 |
| Shin-Etsu AQOAT MF | 0.120 | 0.175 | 0.168 | 0.114 | 0.056 | 0.033 | 0.129 | 0.058 |
| Shin-Etsu AQOAT HF | 0.149 | 0.186 | 0.262 | 0.110 | 0.033 | 0.034 | 0.072 | 0.050 |

TABLE 5A

Percentage of Acetyl and Succinoyl at C6 and C3 Hydroxyl Positions

| Sample | % $C_6 DS_{Ac}$ | % $C_3 DS_{Ac}$ | % $C_6 DS_{Suc}$ | % $C_3 DS_{Suc}$ |
|---|---|---|---|---|
| Polymer 1 | 27 | 34 | 18 | 41 |
| Polymer 2 | 37 | 23 | 1 | 75 |
| Polymer 3 | 33 | 29 | 0 | 73 |
| Polymer 4 | 51 | 16 | 0 | 58 |
| Polymer 5 | 16 | 43 | 36 | 35 |
| Polymer 6 | 20 | 36 | 44 | 30 |
| Polymer 7 | 19 | 47 | 36 | 33 |
| Polymer 8 | 30 | 34 | 22 | 49 |
| Polymer 9 | 28 | 34 | 24 | 40 |
| Polymer 10 | 31 | 26 | 3 | 68 |
| Polymer 11 | 44 | 18 | 0 | 58 |
| Polymer 12 | 33 | 25 | 0 | 75 |
| Polymer 13 | 32 | 29 | 0 | 72 |
| Polymer 14 | 39 | 21 | 0 | 62 |
| Polymer 15 | 37 | 23 | 0 | 62 |
| Polymer 16 | 34 | 24 | 4 | 61 |
| Polymer 17 | 33 | 26 | 0 | 72 |
| Polymer 18 | 44 | 19 | 6 | 67 |
| Polymer 19 | 48 | 15 | 1 | 60 |
| Polymer 20 | 18 | 48 | 38 | 35 |
| Polymer 21 | 20 | 46 | 40 | 33 |
| Polymer 22 | 16 | 46 | 35 | 34 |
| Polymer 23 | 6 | 59 | 48 | 26 |
| Polymer 24 | 15 | 51 | 59 | 18 |
| Polymer 25 | 15 | 50 | 45 | 23 |
| Polymer 26 | 15 | 48 | 53 | 25 |
| Polymer 27 | 22 | 41 | 42 | 25 |
| Shin-Etsu AQOAT LF | 32 | 27 | 13 | 53 |
| Shin-Etsu AQOAT MF | 30 | 29 | 12 | 47 |
| Shin-Etsu AQOAT HF | 26 | 37 | 18 | 38 |

Melt Index Measurement of HPMC-AS

Melt flow index of HPMC-AS was measured using Tinius Olsen Thermodyne 5208. About 5 grams of HPMC-AS powder were loaded to the die and packed to avoid air. A piston was introduced into the die. The die temperature was raised to about 100° C., and was equilibrated for about 5 minutes. Then 5 kilograms of a weight were applied onto the piston, and an extrudate was collected in 6 minutes if there was any. 5 kilograms of the weight was removed from the piston. Then the die temperature was increased by 10° C. and was equilibrated for about 5 minutes. The same procedure was repeated to collect the extrudate at the elevated temperature, until no HPMC-AS left in the die. The extrusion time and the amounts of extrudate were recorded. Melt flow index was calculated as grams of polymer/10 minutes of flow time. Table 6 shows the results.

TABLE 6

Melt Index Result

| Sample | Melt flow Index (grams/10 minutes) | | | | | | | | |
|---|---|---|---|---|---|---|---|---|---|
| | 100-140° C. | 150° C. | 160° C. | 170° C. | 180° C. | 190° C. | 195° C. | 200° C. | 210° C. |
| Polymer 1 | 0 | 0 | 0.1 | 0.6 | 1.78 | 3.88 | — | 8.48 | — |
| Polymer 3 | 0 | 0 | 0.43 | 1.45 | 4.95 | — | — | — | — |
| Polymer 7 | 0 | 0 | 0 | 0 | 1.06 | 1.61 | — | 1.85 | 0.48 |
| Shin-Etsu AQOAT HF | 0 | 0 | 0 | 0.31 | 0.66 | 0.9 | 0.46 | — | — |
| Polymer 2 | 0 | 0.03 | 0.31 | 1.26 | 3.78 | 15.86 | — | — | — |
| Polymer 6 | 0 | 0 | 0 | 0 | 0 | 0 | — | — | — |
| Shin-Etsu AQOAT MF | 0 | 0 | 0 | 1.33 | 0.25 | — | — | — | — |
| Polymer 4 | 0 | 0.03 | 0.3 | 0.96 | 2.03 | 0.1 | — | — | — |
| Polymer 5 | 0 | 0 | 0 | 0 | 0 | 0 | — | — | — |
| Shin-Etsu AQOAT LF | 0 | 0 | 0 | 0.2 | 0.01 | — | — | — | — |

Anti-Nucleating Test

Anti-nucleating test was conducted using the supersaturation method as described previously. 26.3 mg of HPMC-AS was added to 26.3 mL of FASSIF pH=6.5 phosphate buffer in a 2 oz jar. The mixture was either shaken for 5 h in a water bath orbital shaker at 37° C. and 200 shakes/minute or kept overnight at room conditions around 25° C., and warmed up to 37° C. for 1 h before adding the supersaturated nifedipine solution. Nifedipine supersaturated solution was prepared by adding 1.5 grams of nifedipine (solute) to 30 g methanol and using sonication to dissolve the solute. Then 0.79 g of the nifedipine supersaturated solution was added dropwise to the 2-oz jar containing the HPMC-AS and FASSIF within about 30 seconds. The 2-oz jar was continuously shaken at 200 times/minute. 1 mL samples at different time points was taken out, and centrifuged with a minicentrifuge (Minispin Plus®, manufactured by Eppendorf) at 14.5 k rpm for 4 minutes. 0.1 mL supernatant obtained from centrifuge was then added to amber HPLC vials, and diluted with 1 mL methanol. Nifedipine concentration was analyzed using HPLC. Restek Ultra Aqueous C18 column at 40° C. and an isocratic 70/30 water/acetonitrile mobile phase with UV detection at 235 nm were used. Sample aliquots (2 uL) were injected onto the column and eluted at 0.2 mL/min. Nifedipine concentration in each HPLC vial was converted to the concentration of nifedipine in the corresponding 2 oz jar based on the dilution factor and expressed as μg/mL. The experimental results are shown in Table 7.

TABLE 7

Anti-nucleating Results

| Sample | Nifedipine concentration (μg/mL) | | | | | | $AUC_{15,120}$ (μg × min/mL)* |
|---|---|---|---|---|---|---|---|
| | 15 min | 30 min | 60 min | 120 min | 180 min | 240 min | |
| Polymer 1** | 1,272 | 895 | 450 | 299 | 262 | 244 | 58,933 |
| Polymer 3*** | 1,295 | 930 | 459 | 319 | 263 | 251 | 60,932 |
| Polymer 7** | 879 | 674 | 430 | 305 | 275 | 255 | 50,290 |
| Shin-Etsu AQOAT HF*** | 1,021 | 934 | 510 | 289 | 261 | 233 | 60,314 |
| Polymer 2*** | 774 | 674 | 260 | 129 | 101 | 102 | 36,576 |

TABLE 7-continued

Anti-nucleating Results

| Sample | Nifedipine concentration (μg/mL) | | | | | | $AUC_{15,120}$ |
| --- | --- | --- | --- | --- | --- | --- | --- |
|  | 15 min | 30 min | 60 min | 120 min | 180 min | 240 min | (μg × min/mL)* |
| Polymer 6** | 1,166 | 392 | 209 | 162 | 136 | 132 | 31,870 |
| Shin-Etsu AQOAT MF*** | 1,005 | 556 | 312 | 173 | 144 | 129 | 39,361 |
| Polymer 4** | 332 | 142 | 92 | 78 | 76 | 76 | 12,250 |
| Polymer 5*** | 495 | 333 | 133 | 96 | 87 | 98 | 20,132 |
| Shin-Etsu AQOAT LF*** | 397 | 170 | 123 | 97 | 91 | 87 | 15,276 |

*$AUC_{15,120}$ represents area under curve between 15 and 120 minutes
**HPMCAS samples were mixed with FASSIF pH 6.5 and kept overnight at room conditions, and warmed up to 37° C. for 1 hour before adding the supersaturated nifedipine solution.
***HPMCAS and FASSIF pH 6.5 mixtures were shaken for 5 hours in water bath at 37° C. before conducting the supersaturation test.

HPMC-AS Tablet Hardness Test

HPMC-AS powder was screened through a 40 mesh screen. For Shin-Etsu AQOAT HPMC-AS granule grades, the polymers were grounded using a CuisinArt for 30 seconds prior to screening. Then the screened polymers were blended with 1% stearic acid using a Turbula Mixer for 30 seconds, and compressed into 3/18" flat faced bevel edge (FFBE) tablets with 280 mg weight, using a Beta Press. Tablet crushing strengths were measured using a tablet strength tester provided by Key International Inc. All tests were repeated 5 times.

The bulk/tap density of granules was measured using a 10 mL graduated cylinder. The polymer was weighed out prior to loading into the cylinder, and the volume prior to and after the tapping was recorded. The tapping count was 100 times. The experiment was repeated in triplicate.

Particle sizes of granules were analyzed using a Sympatec Helos, a particle size analyzer with laser diffraction for dry particles. The results are shown in Table 8.

TABLE 8

Tablet Compaction

| Sample | Tablet crushing strength (kp) | | | | | Average particle size (μm) | Bulk density (g/mL) | Tap density (g/mL) |
| --- | --- | --- | --- | --- | --- | --- | --- | --- |
|  | 5 (kN) | 10 (kN) | 15 (kN) | 20 (kN) | 25 (kN) |  |  |  |
| Polymer 1 | 23.0 | 30.6 | 35.3 | 38.4 | 37.3 | 155.1 | 0.195 | 0.229 |
| Polymer 3 | 13.7 | 23.8 | 28.8 | 30.9 | 30.7 | 194.9 | 0.312 | 0.352 |
| Polymer 7 | 32.6 | 40.5 | 43.4 | 43.7 | 43.4 | 177.4 | 0.202 | 0.239 |
| Shin-Etsu AQOAT LG | 14.7 | 25.6 | 27.8 | 29.2 | 29.5 | 180.9 | 0.314 | 0.347 |
| Polymer 2 | 25.3 | 37.8 | 42.4 | 43.8 | 43.9 | 177 | 0.214 | 0.247 |
| Polymer 6 | 23.2 | 33.1 | 38.3 | 39.7 | 40.6 | 222.3 | 0.209 | 0.240 |
| Shin-Etsu AQOAT MG | 16.1 | 23.4 | 27.3 | 28.3 | 29.2 | 261.7 | 0.300 | 0.334 |
| Polymer 5 | 23.8 | 30.2 | 33.0 | 34.1 | 34.6 | 187.8 | 0.232 | 0.284 |
| Shin-Etsu AQOAT HG | 9.8 | 13.7 | 15.6 | 16.7 | 16.7 | 194.3 | 0.308 | 0.326 |

Melt Flow Index of HPMC-AS and Nifedipine Mixture

Melt flow index of a mixture of HPMC-AS and nifedipine was measured using Tinius Olsen Thermodyne 5208. Prior to the measurement, HPMC-AS (about 75% by weight) and nifedipine (about 25% by weight) were blended with a Turbula Mixer for about 5 minutes. About 5 grams of the mixture were loaded to the die and packed to avoid air. A piston was introduced into the die. The die temperature was raised to about 100° C., and was equilibrated for about 5 minutes. A weight of 5 kilograms was applied onto the piston, and an extrudate was collected in 6 minutes if there was any. The weight of 5 kilograms was removed from the piston. Then the die temperature was increased by 10° C. and was equilibrated for about 5 minutes. The same procedure was repeated to collect the extrudate at the elevated temperature, until no mixture was left in the die. The extrusion time and the amounts of extrudate were recorded. Melt flow index was calculated as grams of polymer/10 minutes of flow time. Table 9 shows the results.

TABLE 9

Melt Flow Index Results

| Sample | Melt flow Index (grams/10 minutes) | | | | |
| --- | --- | --- | --- | --- | --- |
|  | 120-140° C. | 150° C. | 160° C. | 170° C. | 180° C. |
| Polymer 1 | 0 | 0.06 | 2.08 | 11.73 | — |
| Polymer 3 | 0 | 0.18 | 4.08 | 16.69 | — |
| Polymer 7 | 0 | 0.01 | 0.98 | 5.55 | 8.13 |

TABLE 9-continued

Melt Flow Index Results

| Sample | Melt flow Index (grams/10 minutes) | | | | |
| --- | --- | --- | --- | --- | --- |
|  | 120-140° C. | 150° C. | 160° C. | 170° C. | 180° C. |
| Shin-Etsu AQOAT HF | 0 | 0 | 0.93 | 8.24 | — |

Spray Dried Dispersion (SDD) of HPMC-AS

Spray-drying solutions were prepared by dissolving 5% (w/w) solids (HPMC-AS and drug) into 2:1 (w/w) dichloromethane:methanol solvent (10 g solids+190 g solvent). The ratio of the drug to the HPMC-AS was varied depending on the API. For 50% drug load, 5 g API and 5 g HPMC-AS samples were used. For 60% drug load, 6 g API and 4 g HPMC-AS samples were used. Spray-drying was performed on a GEA SD Micro™ Spray-Dryer (available from GEA Process Engineering A/S, Soeborg, Denmark). The feed material was atomized using a 0.5 mm two-fluid Schlick nozzle targeting an inlet temperature of 85° C., a process gas flow of 25 kg/hr, an atomizing gas pressure of 0.5 bar, and an atomizing gas flow rate of 1.5 kg/hr. The liquid feed rate was adjusted to target an outlet gas temperature of 55° C. After spray-drying, the spray-dried dispersions (spray dried samples) were vacuum dried at 40° C. under −25 in. Hg reduced pressure for 24 hours.

The kinetic solubility of the spray dried sample was measured to demonstrate the superior solubility of dispersions in accordance with the presently disclosed and claimed inventive concept(s) compared to those using Shin-Etsu products and conventional forms without HPMC-AS polymers. Dissolution was performed using a μDISS Profiler™ (available from Pion Inc., MA, USA). Each spray-dried powder was weighed so that the volume adjusted equivalent of the typical daily dose of the drug was added to each vial and compensation was made for the drug load of the samples. For example, the target API was 9.5 mg for Felpdipine in 20 ml of FaSSIF. The spray dried sample containing 9.5 mg API of Felpdipine was weighed. For Ezetimibe, the spray dried sample containing 10 mg API was weighed. The weighed spray dried samples were added to 20 ml of FaSSIF in vials and then heated to 37° C. The vials were maintained at a constant stirring speed of 300 RPM. Dissolution measurements were taken by in situ fiber optic probes at various time points and these measurements were analyzed at the appropriate wavelength for dissolved API concentration. Based on the in situ measurement data, various solubility parameters were calculated.

Spray dried dispersion solubilization results of Felodipine with 50% drug load are listed in Table 10. Spray dried dispersion solubilization results of Ezetimibe with 60% by weight of drug load are shown in Table 11.

TABLE 10

Spray Dried Dispersion (SDD) Solubilization Results with Felodipine

| Sample | $AUC_{120}$[1] (µg × min/mL) | $C_{max}$[2] (µg/mL) | $T_{max}$[3] (min) | $C_{120}$[4] (µg/mL) | AUC (Rel)[5] | $C_{max}$ (Rel)[6] | $C_{120}/C_{max}$[7] |
|---|---|---|---|---|---|---|---|
| Shin-Etsu AQOAT MG | 23,983 | 195 | 91 | 188 | 9.7 | 7.0 | 0.97 |
| Shin-Etsu AQOAT HG | 23,241 | 188 | 111 | 185 | 9.4 | 6.8 | 0.99 |
| Shin-Etsu AQOAT LG | 14,266 | 294 | 2 | 79 | 5.8 | 10.6 | 0.27 |
| Polymer 12 | 25,843 | 221 | 111 | 221 | 10.5 | 8.0 | 1.00 |
| Polymer 13 | 25,140 | 219 | 120 | 219 | 10.2 | 7.9 | 1.00 |
| Polymer 15 | 33,135 | 263 | 120 | 263 | 13.4 | 9.5 | 1.00 |
| Polymer 16 | 30,674 | 242 | 82 | 238 | 12.4 | 8.7 | 0.98 |
| Polymer 17 | 29,102 | 233 | 120 | 233 | 11.8 | 8.4 | 1.00 |
| Polymer 18 | 21,650 | 274 | 7 | 122 | 8.8 | 9.9 | 0.45 |
| Polymer 19 | 19,681 | 278 | 11 | 100 | 8.0 | 10.1 | 0.36 |
| Polymer 23 | 27,004 | 306 | 16 | 145 | 10.9 | 11.0 | 0.47 |
| Polymer 25 | 26,835 | 217 | 101 | 216 | 10.9 | 7.8 | 1.00 |
| Felodipine API | 2,473 | 28 | 120 | 28 | 1.0 | 1.0 | 1.00 |

[1] $AUC_{120}$ = Area Under the Curve (AUC) for API concentration over first 120 minutes of study
[2] $C_{max}$ = Maximum concentration of API in solution over first 120 minutes
[3] $T_{max}$ = Time when $C_{max}$ was achieved
[4] $C_{120}$ = API concentration at time = 120 minutes
[5] AUC(Rel) = Ratio of $AUC_{120}$ of polymer/drug dispersion versus $AUC_{120}$ of API alone
[6] $C_{max}$(Rel) = Ratio of $C_{max}$ of polymer/drug dispersion versus $C_{max}$ of API alone
[7] $C_{120}/C_{max}$ = Ratio of $C_{120}$ versus $C_{max}$ for polymer/drug dispersion or API alone

TABLE 11

Spray Dried Dispersion (SDD) Solubilization Results with Ezetimibe

| Sample | $AUC_{120}$ (µg * min/mL) | $C_{max}$ (µg/mL) | $T_{max}$ (min) | $C_{120}$ (µg/mL) | AUC (Rel) | $C_{max}$ (Rel) | $C_{120}/C_{max}$ |
|---|---|---|---|---|---|---|---|
| Shin-Etsu AQOAT LG | 1,457 | 98 | 2 | 8 | 0.9 | 7.0 | 0.08 |
| Shin-Etsu AQOAT HG | 4,189 | 69 | 4 | 27 | 2.6 | 4.9 | 0.38 |
| Shin-Etsu AQOAT MG | 5,752 | 66 | 6 | 36 | 3.5 | 4.7 | 0.54 |
| Polymer 12 | 9,293 | 84 | 111 | 84 | 5.7 | 6.0 | 1.00 |
| Polymer 13 | 7,865 | 75 | 56 | 54 | 4.8 | 5.4 | 0.71 |
| Polymer 15 | 12,290 | 116 | 34 | 73 | 7.6 | 8.3 | 0.63 |
| Polymer 16 | 13,567 | 115 | 62 | 89 | 8.3 | 8.2 | 0.78 |
| Polymer 17 | 11,565 | 109 | 41 | 63 | 7.1 | 7.7 | 0.58 |
| Polymer 18 | 6,299 | 134 | 4 | 38 | 3.9 | 9.5 | 0.29 |
| Polymer 19 | 4,616 | 137 | 2 | 29 | 2.8 | 9.7 | 0.21 |
| Polymer 23 | 5,280 | 114 | 2 | 34 | 3.2 | 8.1 | 0.30 |
| Polymer 25 | 12,964 | 114 | 60 | 84 | 8.0 | 8.1 | 0.74 |
| Ezetimibe API | 1,626 | 14 | 120 | 14 | 1.0 | 1.0 | 1.00 |

Rheological Measurements of HPMC-AS

The dynamic rheological properties of the HPMC-AS polymers were measured with an AR G2 rheometer with an environmental test chamber (ETC) temperature control system (available from TA Instruments, New Castle, Del., USA). The test geometry was a 25 mm stainless steel parallel plate. Two types of measurement were conducted—isothermal frequency sweep and dynamic temperature ramp. The measurements were carried out under nitrogen atmosphere.

The isothermal frequency sweep was performed at 170° C. The HPMC-AS powder sample was loaded to the test geometry using a sample loading holder. The sample was equilibrated at 170° C. for about two minutes before the test geometry was set to the measurement gap (i.e. 1 mm). The isothermal frequency sweep was conducted with 5 frequencies per decade, between 0.1 and 600 rad/s.

The dynamic temperature ramp was conducted at temperatures ranged from 150° C. to 200° C. The HPMC-AS powder sample was loaded to the test geometry at 170° C. using a sample loading holder. This sample was equilibrated at 170° C. for about two minutes before the test geometry was set to the measurement gap (i.e. 1 mm). After loading, the temperature was lowered to 150° C. under a constant axial force control of 0+/−0.2 N. The sample was then equilibrated at 150° C. for 5 minutes before the measurement. The temperature ramp was programmed from 150° C. to 200° C. at a heating rate of 2° C. per minute. The measurement frequency was set at 6.28 rad/s (i.e. 1 Hz) and the strain was within the linear viscoelastic region of each sample.

Figure 4:
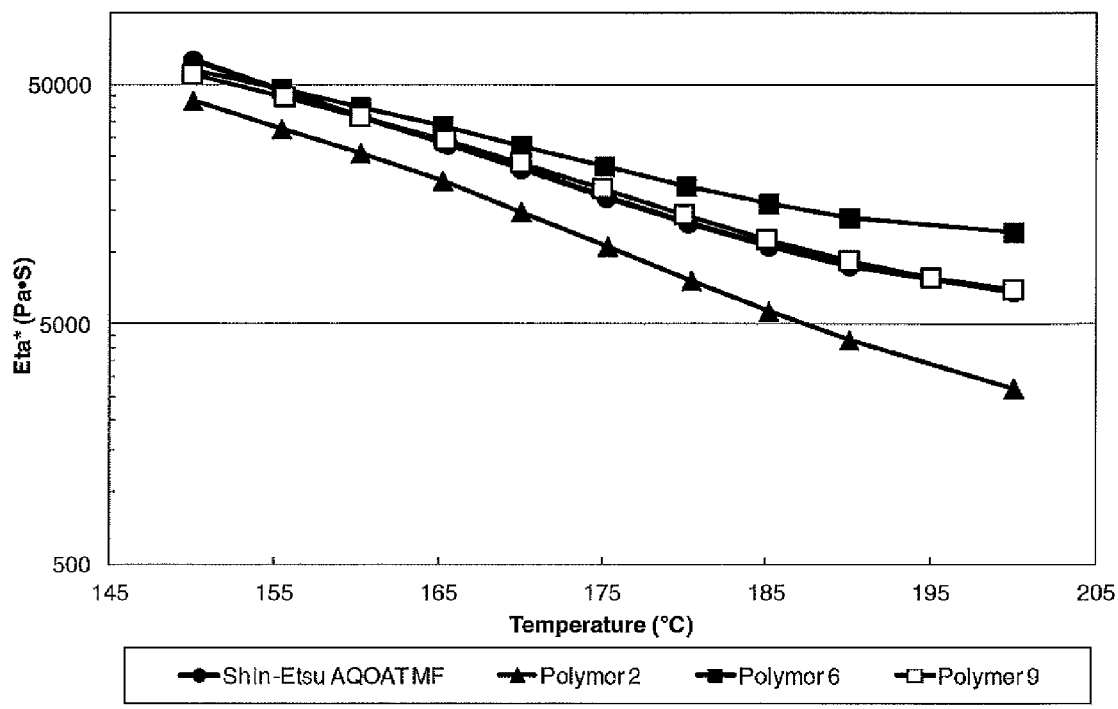
FIG. 4 is a plot showing the dynamic viscosity Eta* versus the temperature for M Grade HPMC-AS samples of Shin-Etsu AQOAT MF, Polymer 2, Polymer 6, and Polymer 9.
Figure 5:
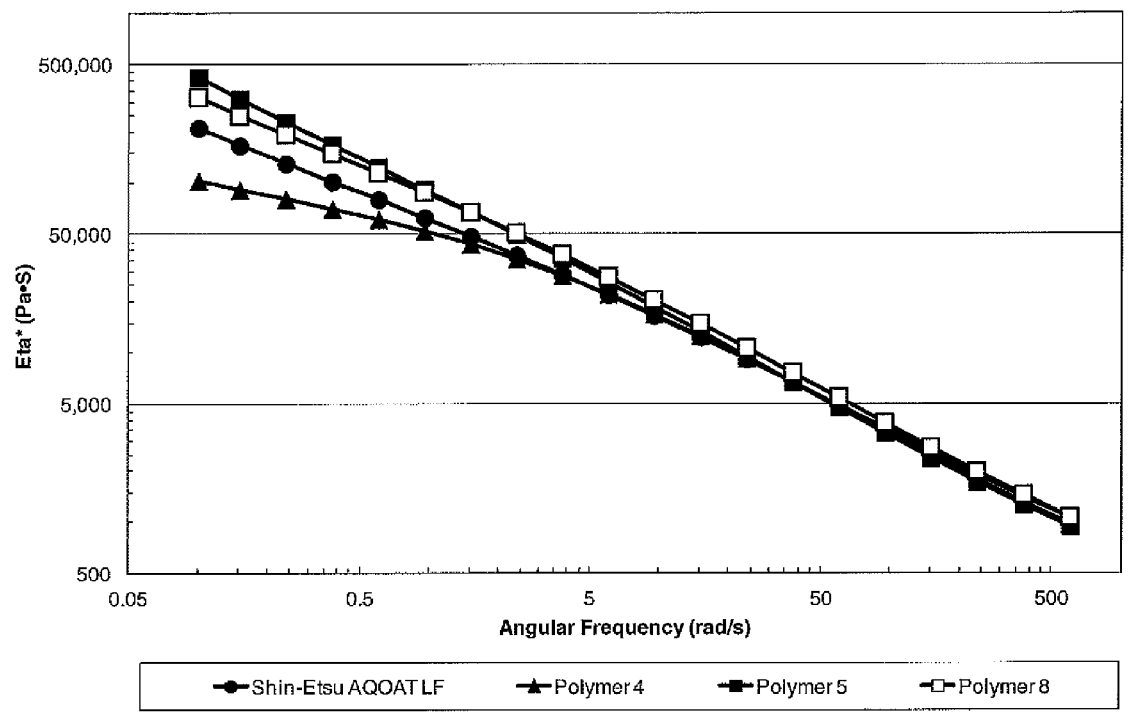
FIG. 5 is a plot showing the dynamic viscosity Eta* versus the angular frequency for L Grade HPMC-AS samples of Shin-Etsu AQOAT LF, Polymer 4, Polymer 5, and Polymer 8.
Figure 6:
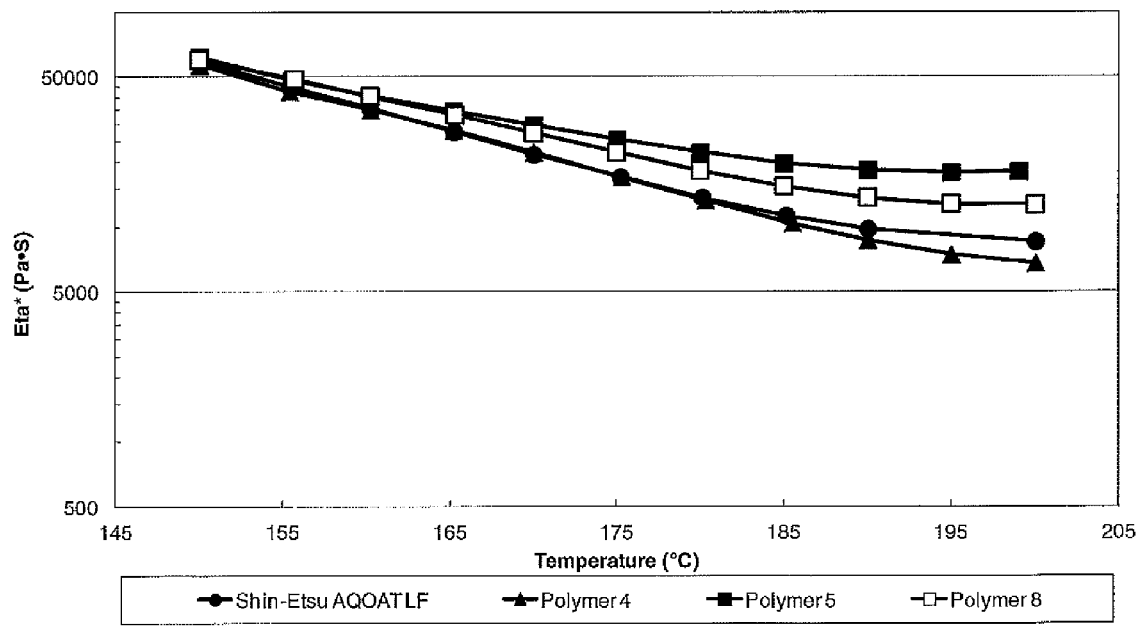
FIG. 6 is a plot showing the dynamic viscosity Eta* versus the temperature for L Grade HPMC-AS samples of Shin-Etsu AQOAT LF, Polymer 4, Polymer 5, and Polymer 8.

The measurement results for the dynamic rheological properties represented in various formats can easily be inter-converted. Starting from the angular frequency ($\omega$) dependent storage modulus $G'(\omega)$ and the loss modulus $G''(\omega)$, the following equations hold (J. D. Ferry, "Viscoelastic Properties of Polymers", John Wiley & Sons, (1980) 3rd Edition):

The dynamic modules $G^*(\omega)=(G'(\omega)^2+G''(\omega)^2)^{0.5}$
The phase angle $\tan\delta=G''(\omega)/G'(\omega)$
The dynamic viscosity $Eta^*(\omega)=G^*(\omega)/\omega$ FIGS. 1, 3 and 5 show the frequency sweep results of HPMC-AS samples with H, M and L grades obtained from various synthesis methods compared with the corresponding Shin-Etsu products with H, M and L grades, respectively. FIGS. 2, 4 and 6 show the temperature ramp results of these samples compared with the corresponding Shin-Etsu products, respectively. For H grade samples, the melt viscosity of Polymer 3 is lower while the melt viscosity of Polymer 7 is higher than those of the Shin-Etsu products. The melt viscosities of Polymer 1 and the Shin-Etsu product are close. For M grade samples, the melt viscosity of Polymer 2 is lower while the melt viscosity of Polymer 6 is higher than those of the Shin-Etsu products. The melt viscosities of Polymer 9 and the Shin-Etsu product are close. For L grade samples, the melt viscosity of Polymer 4 is lower while the melt viscosities of Polymers 5 and 8 are greater than those of the Shin-Etsu products.

Figure 9:
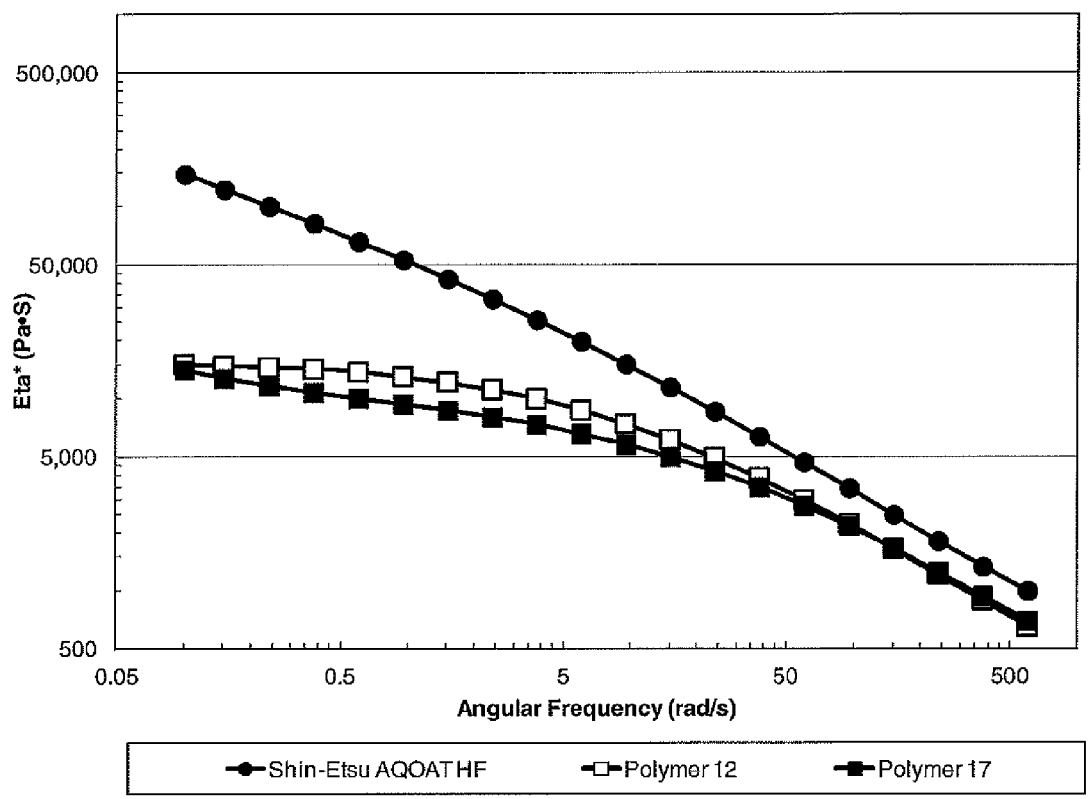
FIG. 9 is a plot showing the dynamic viscosity Eta* versus the angular frequency for H Grade HPMC-AS samples of Shin-Etsu AQOAT HF, Polymer 12, and Polymer 17.
Figure 10:
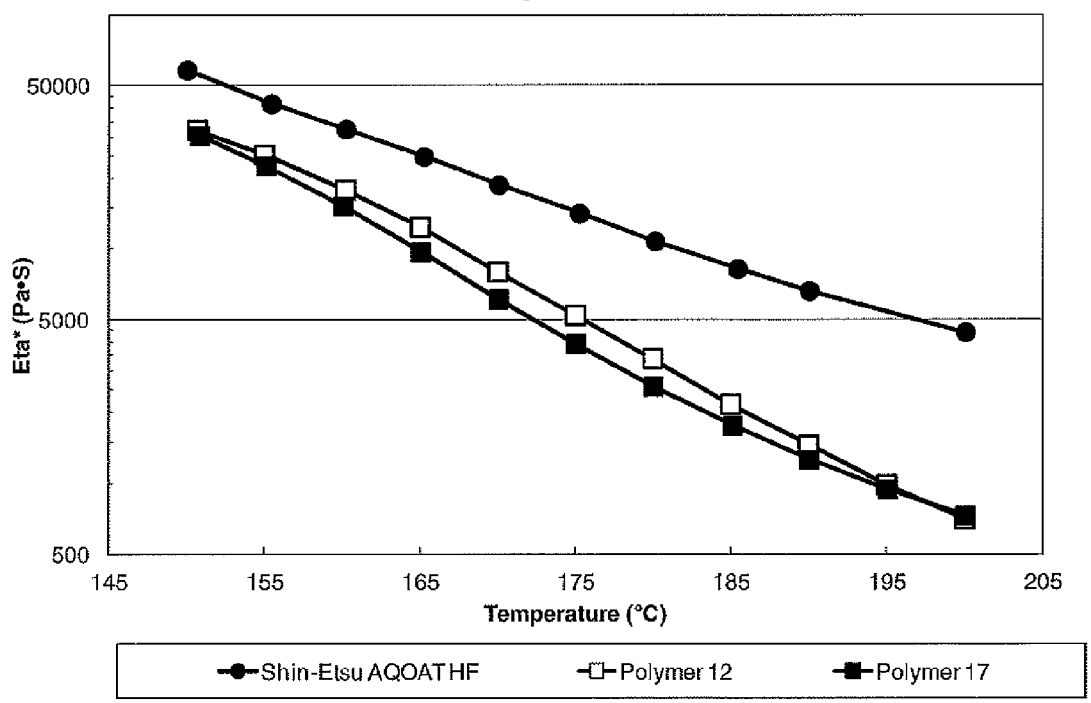
FIG. 10 is a plot showing the dynamic viscosity Eta* versus the temperature for H Grade UPMC-AS samples of Shin-Etsu AQOAT HF, Polymer 12 and Polymer 17.
Figure 13:
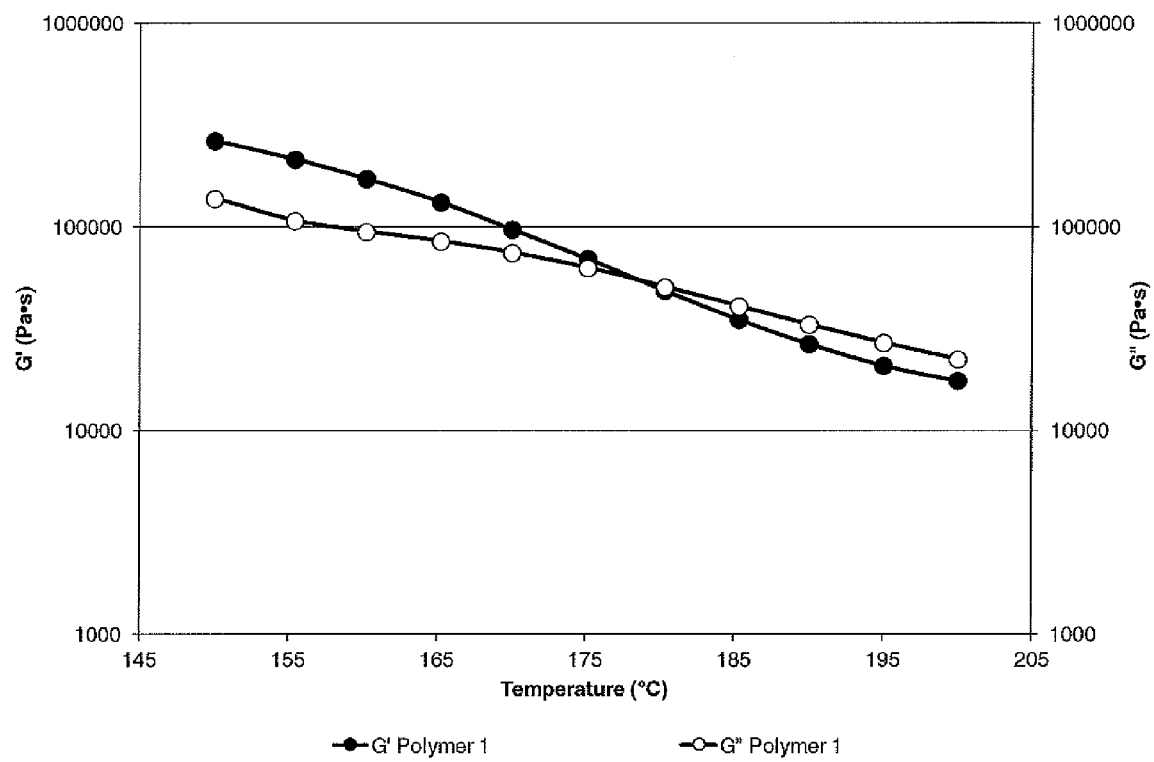
FIG. 13 is a plot showing G' and G" moduli versus the temperature for Polymer 1.
Figure 14:
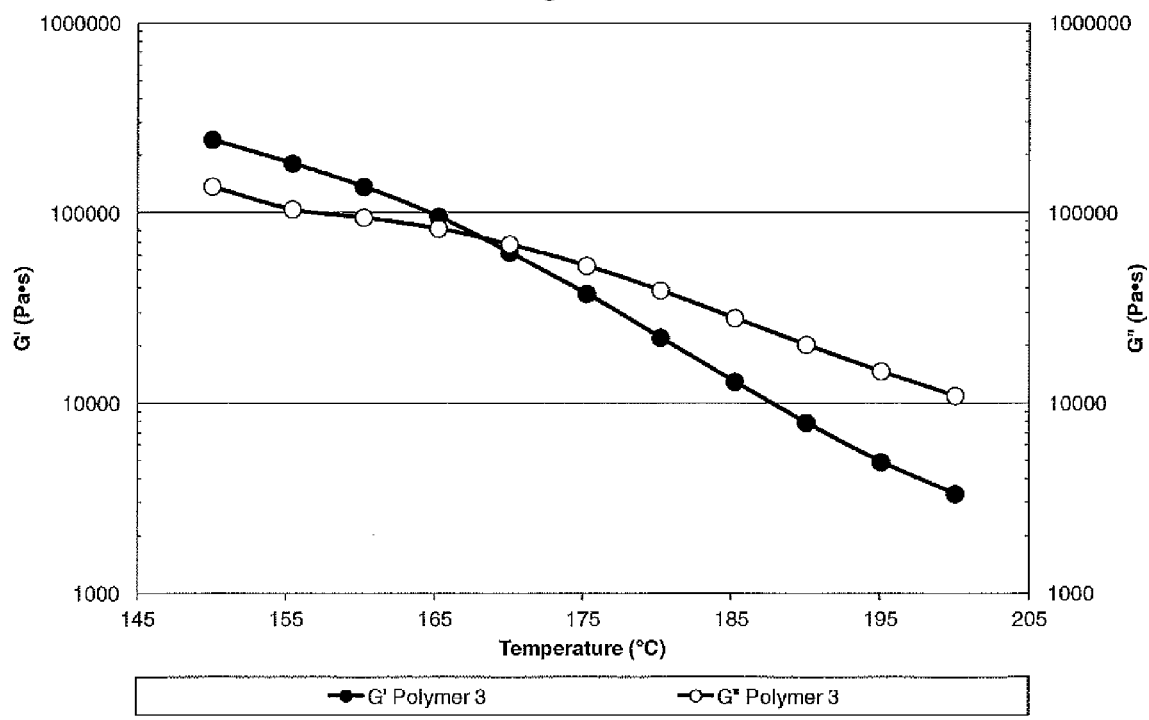
FIG. 14 is a plot showing G' and G" moduli versus the temperature for Polymer 3.

FIGS. 7, 9 and 11 show the frequency sweep results of H Grade HPMC-AS samples with high molecular weight and low molecular weight, and L Grade HPMC-AS samples compared with the corresponding Shin-Etsu products with H and L grades, respectively. FIGS. 8, 10 and 12 show the temperature ramp results of these samples compared with the corresponding Shin-Etsu products, respectively. For H Grade high molecular weight samples, the melt viscosity of Shin-Etsu product is slightly greater than those of Polymer 13 and Polymer 16. For H Grade low molecular weight samples, the melt viscosity of Shin-Etsu product is greater than those of Polymer 12 and Polymer 17. For L grade samples, the melt viscosity of Shin-Etsu product is greater than Polymer 19 but close to Polymer 18.

FIGS. 13-16 show the temperature dependences of the storage moduli G' and the loss moduli G'' of Polymer 1, Polymer 3, Polymer 7 and Shin-Etsu AQOAT HF, respectively. Polymer 1 and Polymer 3 have crossover temperatures at which G' is equal to G''. The crossover temperature of Polymer 1 is higher than that of Polymer 3. There is no observed crossover temperature for Polymer 7 and Shin-Etsu product even though G' is close to G'' as the temperature is increased for the Shin-Etsu product.

It was also found that the HPMC-AS polymers obtained from different synthetic methods have different weight average molecular weight increase when adding acetyl and succinoyl groups on the HPMC polymer. Generally, the percentage increase of the weight average molecular weight of HPMC-AS from Method A is greater than 60%. The percentage increase of the weight average molecular weight of HPMC-AS from Method B is less than 60% while the percentage increase of the weight average molecular weight of HPMC-AS from Method C is greater than 100%.

It is, of course, not possible to describe every conceivable combination of the components or methodologies for purpose of describing the disclosed information, but one of ordinary skill in the art can recognize that many further combinations and permutations of the disclosed information are possible. Accordingly, the disclosed information is intended to embrace all such alternations, modifications and variations that fall within the spirit and scope of the appended claims.

What is claimed is:

1. A polymer for enhancing drug performance and improving processability, wherein the polymer is hydroxypropyl methyl cellulose acetate succinate having:
   a percentage of a total degree of substitution (DS) of succinoyl less than or equal to 6% at a C6-OH position (%$C_6DS_{Suc}$≤6%) and from 58% to 84% at a C3-OH position (58% <%$C_3DS_{Suc}$<84%), and
   a percentage of a total DS of acetyl from 33% to 51% at a C6-OH position (33%<%$C_6DS_{Ac}$<51%) and from 16% to 20% at the C3-OH position (16%<%$C_3DS_{Ac}$<20%).

2. A composition comprising a drug and a polymer, wherein the polymer is hydroxypropyl methyl cellulose acetate succinate having:
   a percentage of a total degree of substitution (DS) of succinoyl less than or equal to 6% at a C6-OH position (%$C_6DS_{Suc}$≤6%) and from 58% to 84% at a C3-OH position (58%<%$C_3DS_{Suc}$<84%), and
   a percentage of a total DS of acetyl from 33% to 51% at a C6-OH position (33%<%$C_6DS_{Ac}$<51%) and from 16% to 20% at the C3-OH position (16%< %$C_3DS_{Ac}$<20%).

3. The composition of claim 2, wherein the drug is a low-solubility drug having a solubility equal to or less than about 0.5 mg/mL in an aqueous solution at a pH from 1 to 8.

4. The composition of claim 3, wherein the composition comprises a solid amorphous dispersion comprising the low-solubility drug and the polymer.

5. The composition of claim 3, wherein the composition comprises a physical mixture of the low-solubility drug and the polymer.

\* \* \* \* \*